United States Patent
Head

(10) Patent No.: US 8,454,619 B1
(45) Date of Patent: Jun. 4, 2013

(54) PROSTHETIC SOCKET ALIGNMENT

(76) Inventor: William C. Head, McKinney, TX (US)

( * ) Notice: Subject to any disclaimer, the term of this patent is extended or adjusted under 35 U.S.C. 154(b) by 35 days.

(21) Appl. No.: 12/692,449

(22) Filed: Jan. 22, 2010

Related U.S. Application Data

(63) Continuation-in-part of application No. 12/371,308, filed on Feb. 13, 2009, which is a continuation-in-part of application No. 12/332,109, filed on Dec. 10, 2008, now abandoned.

(60) Provisional application No. 61/296,599, filed on Jan. 20, 2010.

(51) Int. Cl.
- *A61B 17/58* (2006.01)
- *A61B 17/60* (2006.01)
- *A61F 2/00* (2006.01)

(52) U.S. Cl.
USPC .......................................................... 606/91

(58) Field of Classification Search
USPC ........................................ 606/91, 96–99, 104
See application file for complete search history.

(56) References Cited

U.S. PATENT DOCUMENTS

| | | | |
|---|---|---|---|
| 5,030,219 A | 7/1991 | Matsen et al. | |
| 5,953,683 A | 9/1999 | Hansen et al. | |
| 6,156,069 A | 12/2000 | Amstutz | |
| 6,245,111 B1 | 6/2001 | Shaffner | |
| 7,433,798 B2 | 10/2008 | Townsend et al. | |
| 2003/0130741 A1 | 7/2003 | McMinn | |
| 2005/0107799 A1* | 5/2005 | Graf et al. | 606/91 |
| 2006/0058886 A1 | 3/2006 | Wozencroft | |
| 2008/0021479 A1 | 1/2008 | Penenberg | |
| 2008/0196911 A1* | 8/2008 | Krapf et al. | 173/4 |
| 2009/0099665 A1* | 4/2009 | Taylor et al. | 623/22.21 |
| 2010/0114237 A1 | 5/2010 | Giftakis et al. | |
| 2010/0137869 A1 | 6/2010 | Borja et al. | |
| 2010/0137871 A1* | 6/2010 | Borja | 606/91 |

OTHER PUBLICATIONS

Microstrain ADIS16209 High Accuracy, Dual-Axis Digital Inclinometer and Accelerometer product information, Rev. A. Jan. 30, 2008, 17 pgs, Microstrain, Inc., Norwood, MA.
Jonathan, B., "How Does an Inclinometer Work?," Ezine @rticles, http://ezinearticles.com/?How-Does-An-Inclinometer-Work?&id=276738, Aug. 22, 2006, pp. 1-5.
Gehring, J., "Gravity Inclinometer," The Tool Shed, http://www.craftsofnj.org/toolshed/articles/Gravity%20inclinometer/GRAVITY%20INCLINOMETERS.htm, Crafts of New Jersey, Feb. 2002, pp. 1-6.
GlobalSpec Engineering Search Engine, search results for "Tilt Sensors and Inclinometers," http://sensors-transducers.globalspec.com/Industrial-Directory/Tilt_Sensors_and_Inclinometers, search run Feb. 6, 2009, pp. 1-5.
Definition of "Inclinometer," Wikipedia, http://en.wikipedia.org/wiki/Inclinometer, Jan. 27, 2009, pp. 1-3.
Hussain, B., "How Does an Inclinometer Work?," https://www.amazines.com/article_detail.cfm/145829?articleid=145829, Aug. 31, 2006, pp. 1-4.

* cited by examiner

*Primary Examiner* — Sameh Boles

(57) ABSTRACT

Methods, systems and devices for properly positioning and aligning a prosthetic socket and/or prosthetic ball into host bone structure of a patient using one or more guide are shown. Guides implemented according to embodiments may provide reference guidance (e.g., baseline or relative positioning), physical guidance (e.g., restricted movement or physically direct positioning), visual guidance (e.g., visual indication of proper or improper positioning), and combinations thereof. Embodiments comprise placing a guide piece, in bone that is close to the bone cavity, according to the position and alignment of a trial prosthetic socket previously fitted in a desired position and alignment in the bone cavity and then, after removing the trial, positioning and aligning the prosthetic socket in the bone cavity using the guide piece's position and alignment for guidance.

11 Claims, 27 Drawing Sheets

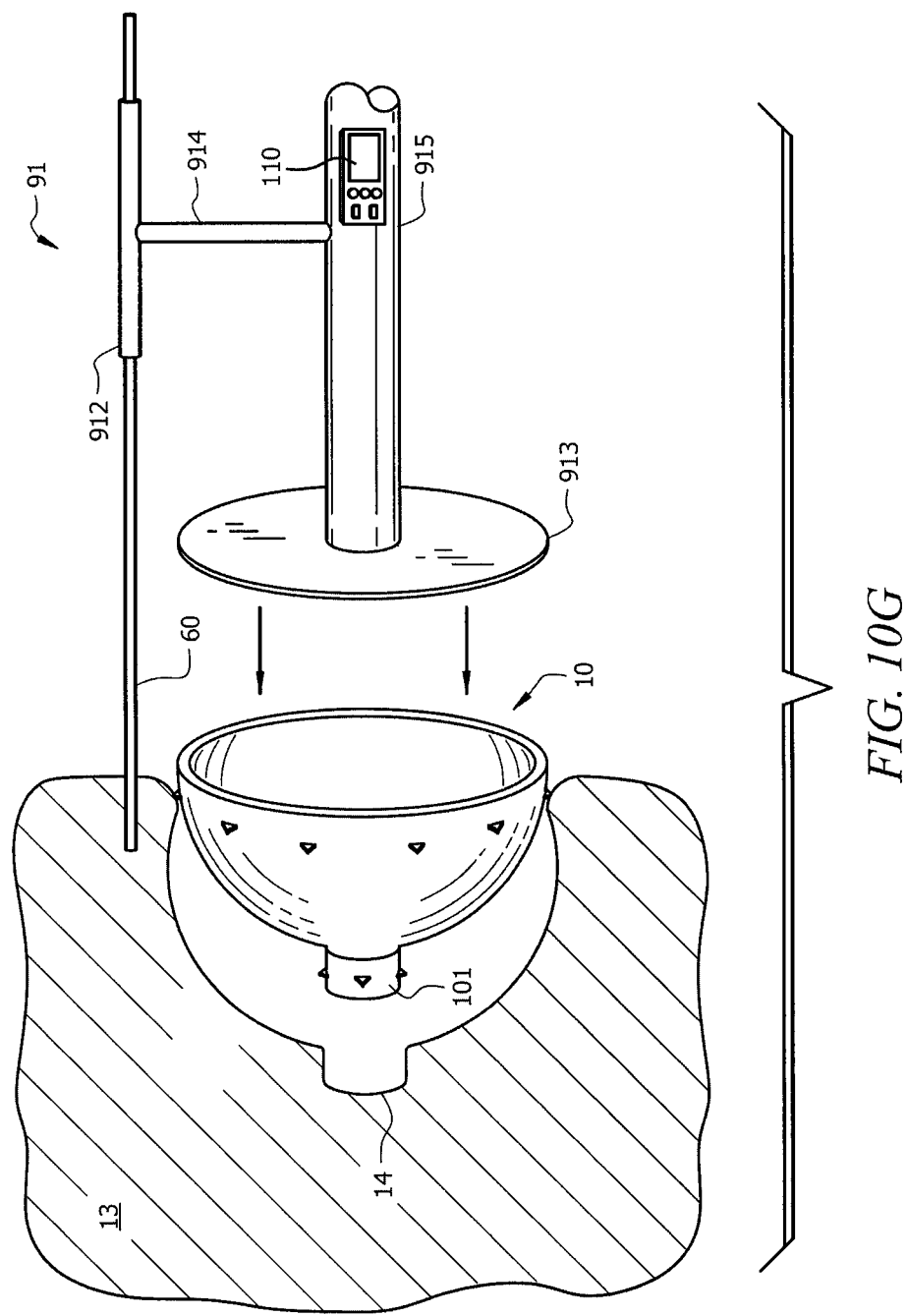

PROSTHETIC SOCKET ALIGNMENT

CROSS-REFERENCE TO RELATED APPLICATIONS

This application claims priority to U.S. Provisional Patent Application No. 61/296,599, entitled "PROSTHETIC SOCKET ALIGNMENT," filed Jan. 20, 2010 and this application is a continuation-in-part of U.S. patent application Ser. No. 12/371,308, entitled "PROSTHETIC SOCKET ALIGNMENT," filed Feb. 13, 2009, which itself is a continuation-in-part of U.S. patent application Ser. No. 12/332,109, entitled "PROSTHETIC SOCKET ALIGNMENT," filed Dec. 10, 2008, now abandoned and is related to co-pending, commonly owned U.S. patent application Ser. No. 12/360,512, entitled "SYSTEM AND METHOD FOR RESURFACING HIP REPLACEMENT," filed Jan. 27, 2009, the disclosures of which are hereby incorporated herein by reference.

TECHNICAL FIELD

The current invention is in the field of prosthetic devices. In particular, the current invention involves the proper alignment of prosthetic devices.

BACKGROUND OF THE INVENTION

A prosthetic device is an artificial device used to replace a body part. For example, since the 1960's, prosthetic devices have been used in hip replacement surgery. Hip replacement surgery is an increasingly common surgery used to treat joint failure in patients. Joint failures are often caused by diseases such as osteoarthritis, rheumatoid arthritis etc. Treating joint failures by hip replacement typically involves replacing the ball on the femur (the bone that extends from the pelvis to the knee) with a prosthetic ball and replacing the socket in the hip with a prosthetic socket. The socket is part of the pelvis and the ball fits into the socket.

Though medical practitioners have been performing hip replacement surgeries for more than half a century, at least two significant problems persist with this medical procedure. First, the prosthetic ball sometimes dislocates from the prosthetic socket (i.e., the prosthetic ball comes out of the prosthetic socket). Improper alignment of the prosthetic ball and socket during hip replacement surgery is one factor that causes dislocation of the prosthetic ball from the prosthetic socket after surgery. Second, depending to some extent on the materials used to make the prosthetic ball and socket, excessive wear of those materials may occur as the prosthetic ball moves in the prosthetic socket during use. As with the dislocation problems, improper alignment of the ball and socket during surgery is one major factor that causes excessive wear during use. For example, excessive wear occurs when the prosthetic ball rubs excessively on one edge of the socket. This is known as edge loading. Wear debris, such as formed by edge loading in the joint, can cause major complications such as inflammation and loosening of the prosthetic components. Moreover, when the prosthetic components wear out or loosen, they have to be replaced in another hip replacement surgery.

Because of the problems associated with improperly aligned prosthetic sockets and balls, medical practitioners generally make every effort to try and properly align these devices during surgery. Most medical practitioners rely on their experience to view the bone cavity and manually place the prosthetic socket in the proper position. For example, the proper alignment of the hemispherical socket in the acetabula (the cup-shaped cavity in the pelvis into which the ball-shaped head of the femur fits) is typically attained when it is about 40° to 45° of abduction. Additionally, when the prosthetic socket is properly aligned in the acetabula, the open area of the socket typically should be about 10° to 20° of anteversion, i.e., facing forward. It should be noted that though the abduction angle is typically about 40° to 45° and the anteversion angle is typically about 10° to 20°, variations outside these ranges are possible and the embodiments of the invention disclosed herein may be used in instances outside of the typical ranges.

Particularly because medical practitioners are now doing surgeries with smaller incisions than have traditionally been used, it is not uncommon that manual fitting of a prosthetic socket during hip surgery results in the prosthetic socket being placed at an angle of 50° to 60° and even facing slightly backward (retroversion). Such improper alignment generally results in dislocations of the hip and excessive wear of the prosthetic ball and socket after surgery. To improve upon manual alignment of prosthetic sockets, medical practitioners have tried to use positioning devices based on x-ray, fluoroscopy, MRI and other electronic technology. Despite these technologies, improper alignments of prosthetic balls and sockets persist and these improper alignments in turn cause complications such as dislocations and excessive wear. Moreover, apart from the limited success with the current positioning devices, these devices are expensive to make and operate.

BRIEF SUMMARY OF THE INVENTION

The present invention is directed to systems, devices and methods which properly position and align a prosthetic socket and/or prosthetic ball in host bone structure using one or more guide. Guides implemented according to embodiments may provide reference guidance (e.g., baseline or relative positioning), physical guidance (e.g., restricted movement or physically direct positioning), visual guidance (e.g., visual indication of proper or improper positioning), and combinations thereof.

Embodiments of the invention implement a reference guide for aligning a prosthetic of a patient by placing a guide piece in bone, such as the pelvic bone, in a predetermined position to establish a baseline reference for use throughout a prosthetic implant procedure. For example, a reference guide of embodiments may comprise a pin which is placed so as to be perpendicular to the operating table when the patient is positioned in the lateral position in preparation for surgery. Such a reference guide is preferably placed (e.g., in the pelvic brim) early in the surgery, such as prior to performing any part of the prosthetic implant procedure, to establish a baseline reference for use throughout the procedure. Reference may be made to the reference guide prior to positioning a prosthetic device, prior to making or using measurements for positioning a prosthetic device, etc. to ensure that the patient has not moved and thus proper prosthetic device is being achieved. Additionally or alternatively, reference may be made to the reference guide as a fixed point for measurement and reference when performing the prosthetic implant procedure.

Embodiments of the invention additionally or alternatively implement a physical guide for aligning a prosthetic of a patient by placing a guide piece in bone, such as the pelvic bone, that is close to the desired position of the prosthetic device (e.g., bone cavity for a prosthetic socket). The position and alignment of a trial prosthetic (hereinafter a "trial"), such as a trial prosthetic socket, is fitted in a desired position and alignment and the physical guide is placed in bone in accordance with the trial position. The bone in which the physical guide is placed may be in or near the bone into or onto which the prosthetic device is to be placed (e.g., in or near the bone cavity for a prosthetic socket). After removing the trial, positioning and aligning of the prosthetic device, such as a prosthetic socket into the bone cavity, is provided using the physical guide piece's position and alignment for physical guidance.

Embodiments of the invention further additionally or alternatively implement a visual guide for aligning a prosthetic of a patent. For example, a tilt (e.g., pitch and/or yaw) sensing device may be disposed upon or provided for use with one or more tools and devices used in a prosthetic implant procedure. In some embodiments of the invention, the visual guide is used to show the tilt angle of devices used in the positioning and alignment procedure, thus providing visual guidance with respect to positioning the prosthetic device. For example, a visual guide comprising the aforementioned tilt sensing device may be used in positioning and aligning the trial, for positioning a reamer during preparation of the bone to receive the prosthetic device, for guiding a prosthetic driver tool used in positioning a prosthetic device, etc.

In operation according to an embodiment of the invention, proper positioning and alignment of a prosthetic socket involves creating a peg positioning bore in the bone using the trial to define the position and alignment of the peg positioning bore. The drill creating the peg positioning bore may comprise a visual guide, such as a tilt sensing device, to provide additional guidance for the position and alignment of the peg positioning bore. A peg of the prosthetic socket of this embodiment is then fitted into the peg positioning bore to help hold the prosthetic socket in the desired position and alignment. In addition to the peg positioning bore, a visual guide, such as the aforementioned tilt sensing device, on a prosthetic socket driver or on a guiding device used to place and/or secure the prosthetic socket in the bone cavity, guides proper positioning and alignment of the prosthetic socket into the bone cavity. Similarly, a visual guide, such as a tilt sensing device, on the reamer or on drill operating the reamer guides proper positioning and alignment of the reamer for preparing the bone cavity for receiving the prosthetic socket in the desired position.

In one embodiment of the invention, proper positioning and alignment includes creating the peg positioning bore in the bone forming the bone cavity. The position of the peg positioning bore is guided by a drill guide channel in the trial. A physical guide (e.g., drill guide) is then placed in the peg positioning bore. The placing of the physical guide may be done with the aid of a visual guide (e.g., tilt sensing device) attached to the physical guide. The physical guide providing drill guidance according to embodiments is a cannulated tube and sleeve and may be made of metal such as a cobalt/chrome alloy. "Cannulated" herein means to have an appropriately sized lumen. A guide piece such as a Kirschner wire is then placed through the cannulated portion of the physical guide and drilled or pushed into the bone. The lumen of the cannulated physical guide is sized to correspond to the guide piece (the lumen is just big enough to allow the guide piece to pass through the physical guide). Thus, the angle in which the guide piece is placed into the bone is defined by the physical guide. This angle will be the same angle the trial was in when properly positioned. The physical guide and trial are then removed leaving the guide piece in the bone.

To position the prosthetic socket of the foregoing embodiment in the exact location and angle as the trial (when the trial was fitted in the bone cavity) a peg (having a lumen sized to correspond to the guide piece) of the prosthetic socket is slid over the guide piece and the peg fitted into the peg positioning bore. Properly positioned by guidance of the guide piece and the peg in the peg positioning bore, the prosthetic socket is securely fastened to the bone by driving it in place using a prosthetic socket driver. The prosthetic socket driver may have a hollow portion so that it may be used while the guide piece is still in place. Additionally, in some embodiments, the prosthetic socket driver may comprise a visual guide, such as a tilt sensing device, or other guide herein to ensure the prosthetic socket is being driven exactly in a direction to achieve the desired position. The force applied to the prosthetic socket of embodiments causes fins on the prosthetic socket to enter the bone and secure the prosthetic socket to the bone.

In another embodiment of the invention, the trial is placed in the bone cavity using a visual guide that comprises a tilt sensing device. Then, a peg positioning bore is created in the bone forming the bone cavity using a physical guide, such as a drill guide channel, in the trial as a guide. A visual guide (e.g., tilt sensing device) attached to the drill that is used to create the peg positioning bore may provide additional guidance for creating the peg positioning bore. As such, the physical guide in the trial and the drill's visual guide is used to establish the angle of the peg positioning bore being drilled in the bone. A modular extension of the physical guide is then fitted in the peg positioning bore. A visual guide, such as the aforementioned tilt sensing device, is again used to ensure the guiding device is positioned in a particular direction according to embodiments.

Various tools used in a prosthetic implant procedure of embodiments of the invention, such as the modular extension of the physical guide of the foregoing embodiment, implement a physical guide (e.g., tubular pin guide), such as a Steinman pin guide, fixedly attached to the guiding device. A guide piece may be drilled or pushed into bone close to the bone cavity using this physical guide (e.g., tubular pin guide) for guidance according to embodiments. The angle in which the guide piece is placed into the bone is established using the physical guide (e.g., tubular pin guide), which is disposed in a predetermined relative position such as precisely parallel to the peg positioning bore. Additional guides, such as a visual guide, such as a tilt sensing device, of the guiding device may be used.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWING

For a more complete understanding of the present invention, reference is now made to the following descriptions taken in conjunction with the accompanying drawing, in which:

FIGS. 3A-3E show trials according to embodiments of the invention;

FIGS. 10A-10G show operation of guide devices used to position and align a prosthetic socket according to an embodiment of the invention;

DETAILED DESCRIPTION OF THE INVENTION

Figure 1A:
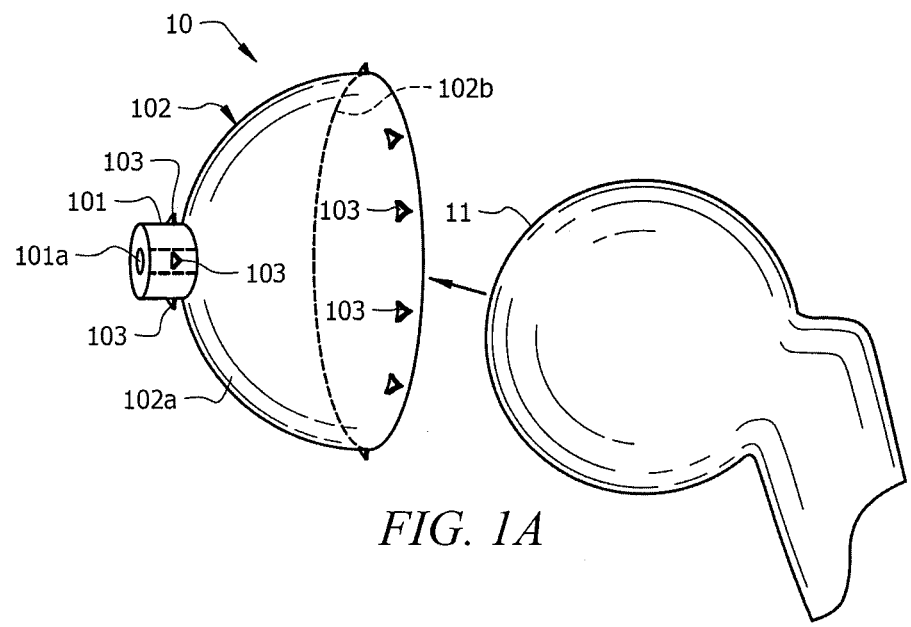
FIG. 1A shows a prosthetic socket and ball according to an embodiment of the invention.
Figure 1B:
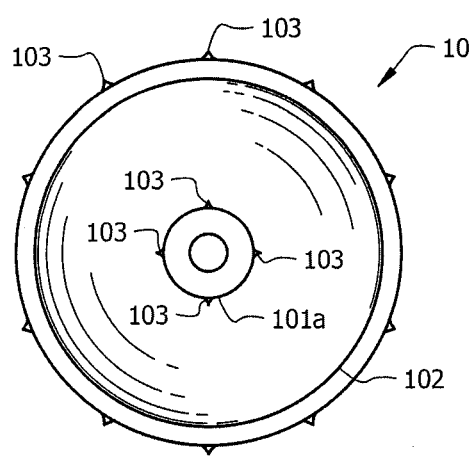
FIG. 1B shows a prosthetic socket according to an embodiment of the invention.

FIGS. 1A and 1B show a prosthetic socket 10 and a prosthetic ball 11 according to one embodiment of the invention. Prosthetic socket 10 may include a peg 101. Peg 101 may have a lumen 101a. Prosthetic socket 10 also has a hemispherical portion 102. Hemispherical portion 102 has an outer portion 102a that fits into the bone cavity of a patient. The inner portion 102b of hemispherical portion 102 receives prosthetic ball 11. Outer portion 102a may have fins 103 for securing prosthetic socket 10 to bone. Peg 101 may also include fins 103 to help secure peg 101 to bone. Prosthetic socket 10 may be made from material such as metal, composites, plastic or ceramic. The composites may comprise materials such titanium, titanium compounds, polymers, carbon nanotubes and the like. Prosthetic ball 11 may be made of metal or ceramic. Outer portion 102a is rough and thereby specially adapted to facilitate bone growth into prosthetic socket 10 to help hold prosthetic socket 10 in place. Typically, the metal used in the prosthetic devices is titanium because titanium is very compatible with bone.

Figure 8A:
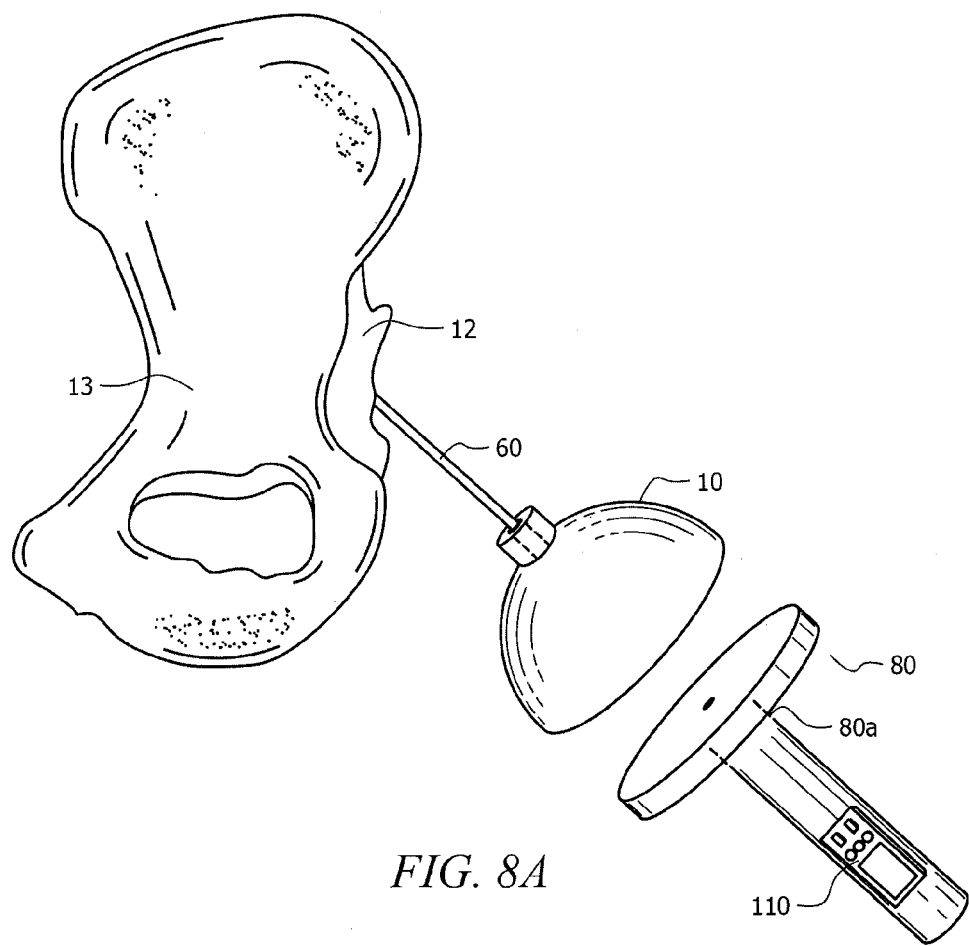
FIGS. 8A and 8B show how a prosthetic socket is fitted to the acetabular region using a driving plate and a cannulated shaft according to embodiments of the invention.
Figure 8B:
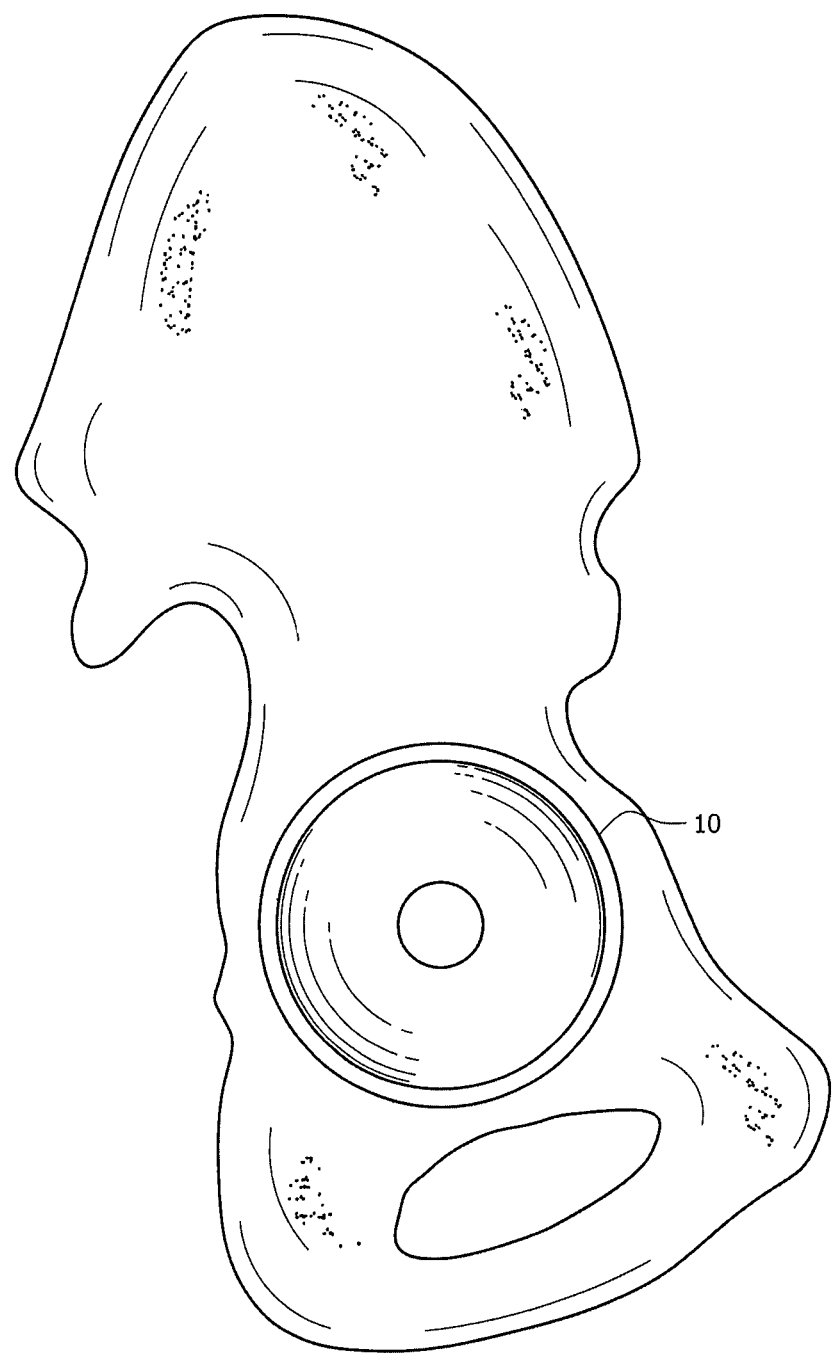

In some cases both the prosthetic ball and socket are metal. In other cases, the prosthetic socket is metal lined on the inner side with plastic or ceramic. Thus, the lining interfaces with prosthetic ball 11. The prosthetic ball may be metal or ceramic. Various combinations are possible and the concepts of the present invention are applicable to all these combinations (e.g., metal ball on metal socket, metal ball on plastic socket, ceramic ball on ceramic socket and ceramic ball on plastic socket). For hip replacement surgery, the prosthetic socket 10 is placed into the bone cavity 12 of the hip bone 13 (FIGS. 8A and 8B). Prosthetic ball 11 is then fitted into prosthetic socket 10. The hip replacement surgery also involves attaching prosthetic ball 11 to the femur or the thigh bone of the patient.

Figure 2:
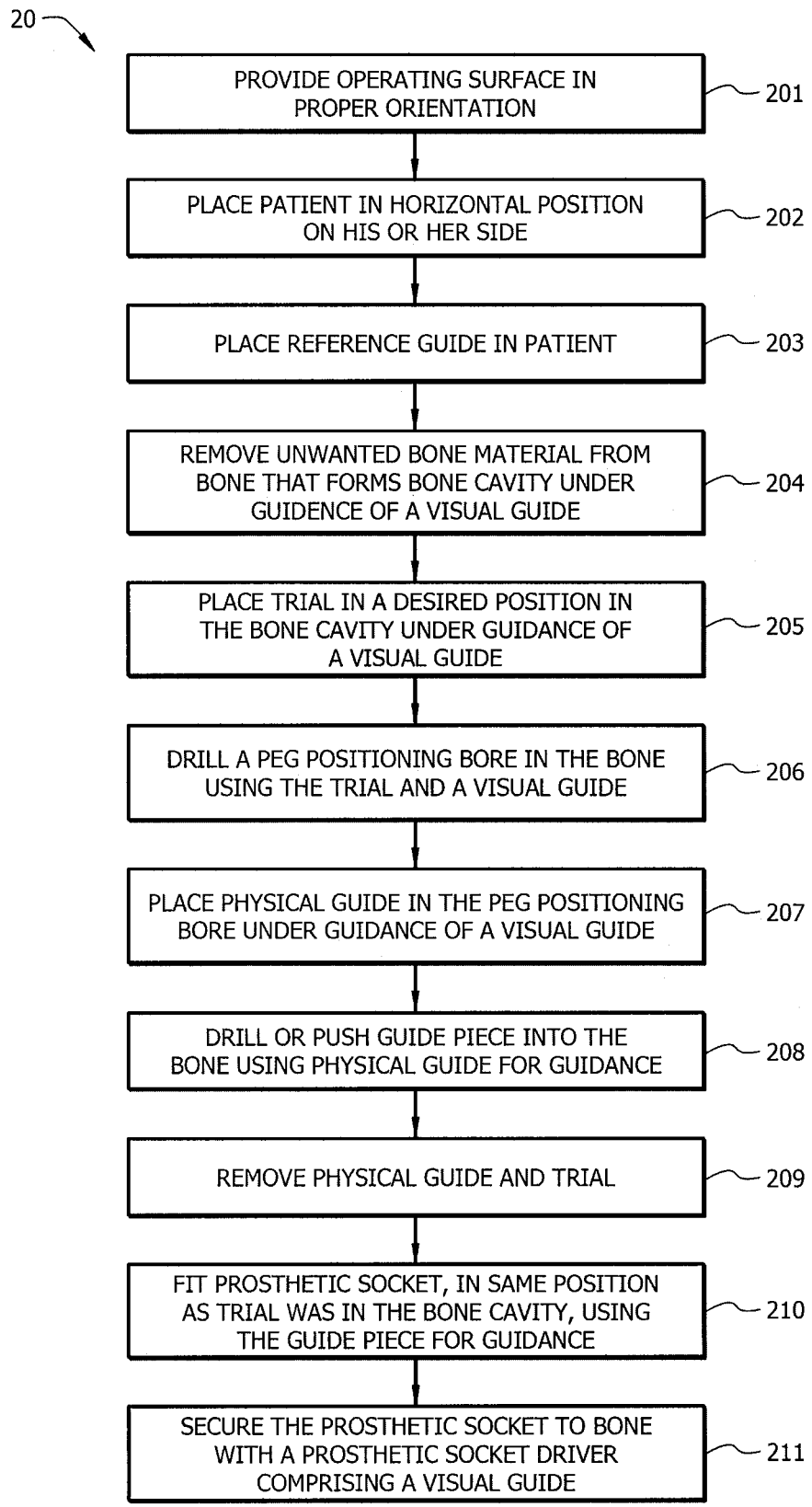
FIG. 2 shows a process to properly align a prosthetic socket using guides according to an embodiment of the invention.

FIG. 2 shows flow 20 of one embodiment of the invention which is a process to properly fit a prosthetic socket within a bone cavity of a patient. It should be appreciated that an expected orientation of the prosthetic socket in the patient's bone cavity may be determined in pre-operative analysis. For example, pre-operation images (e.g., x-ray images, magnetic resonance imaging (MRI) images, ultrasound images, computed tomography (CT) images, etc.) of the patient may be studied to determine the abduction angle and the anteversion angle the prosthetic socket is expected to be disposed in. The desired abduction and antevsion angles of the prosthetic socket may be determined and maintained as a trial and/or the prosthetic socket is being placed in the patient using one or more guides of the present invention. It should be appreciated that the expected abduction and anteversion angles may be modified during an prosthetic implant procedure, such as by placing a trial in a desired position and determining its abduction and anteversion angles using one or more guides herein.

In process 201 of flow 20 of the illustrated embodiment, the operating surface upon which a patient is to be disposed during the prosthetic socket implant procedure is placed in, or confirmed to be disposed in, a proper orientation. For example, to ensure the patient is horizontal, the examination or operating table and floor should be horizontal and level (e.g., the plane of the surface thereof providing a horizontal surface with no tilt). Accurately disposing the patient in a horizontal position is desired according to embodiments in order to establish a proper baseline reference guide, to facilitate use of various visual guides, etc. The operating table or other surface may be provided with a position guide, such as level 1410 shown in FIG. 14B, for use in placed in a proper or desired orientation.

Figure 14A:
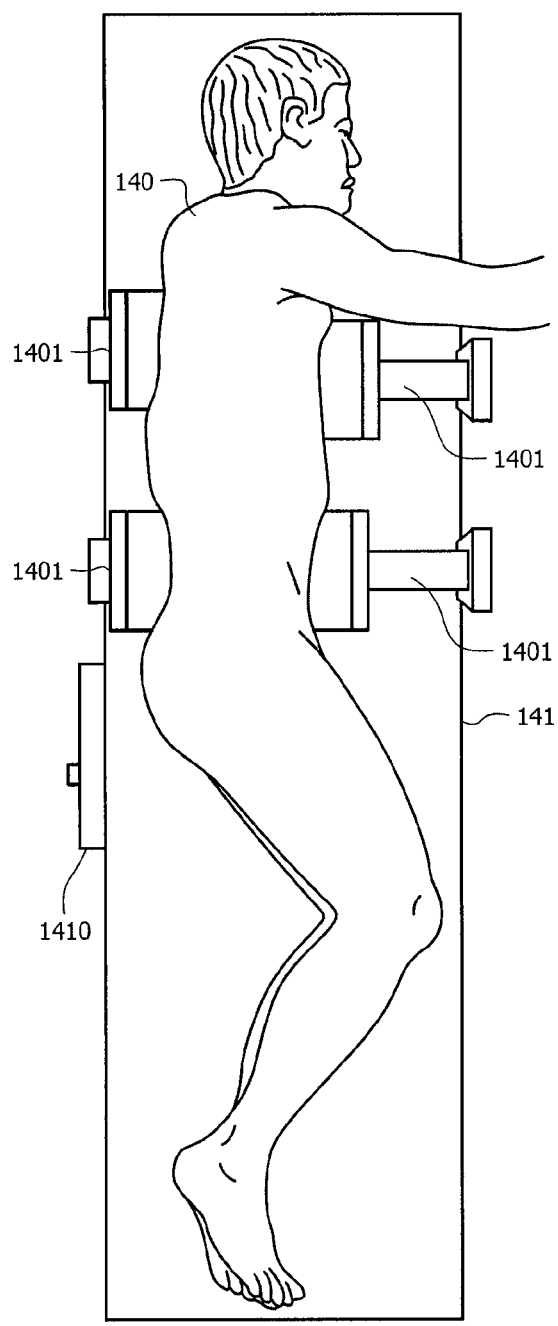
FIGS. 14A and 14B show a patient disposed for performing an implant procedure using guides of embodiments of the invention.
Figure 14B:
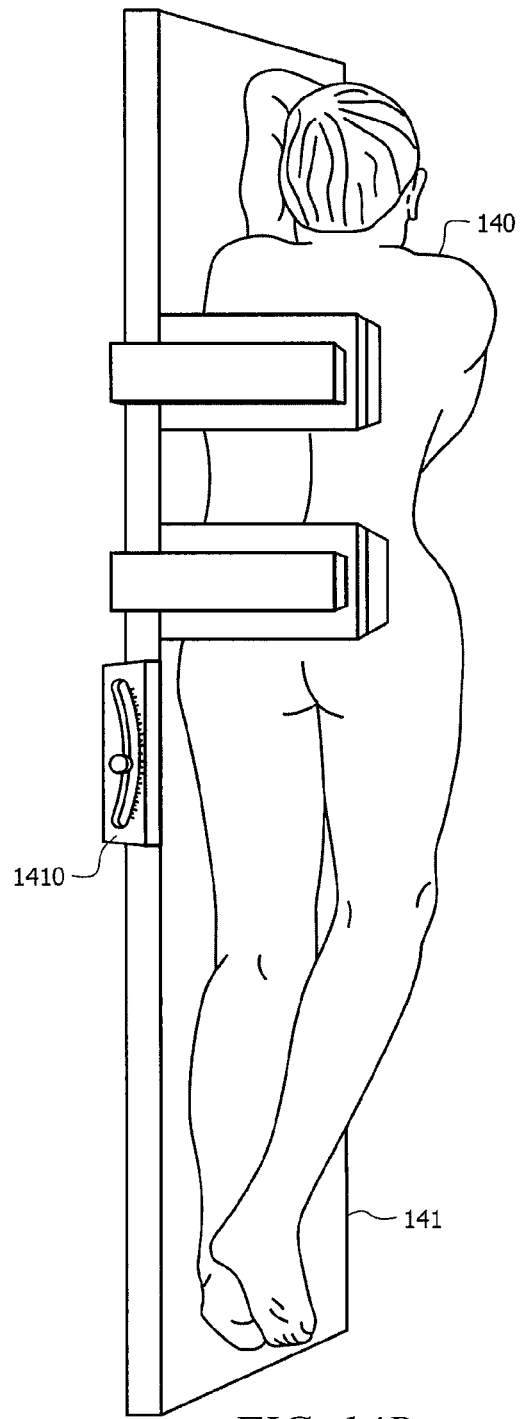

In process 202 of the illustrated embodiment, patient 140 is positioned horizontally on his or her side on operating surface 141 as shown in FIGS. 14A and 14B. According to a preferred embodiment, the patient is positioned so as to have their back perpendicular to the operating surface. Positioning devices, such as positioning devices 1401 shown in FIGS. 14A and 14B, may be utilized to encourage a patient to remain in a desired position (e.g., the aforementioned horizontal position) during all or some part of the procedure. For example, padded bolsters may be adjustably attached to operating surface 141 for use as positioning devices when patient 140 has been positioned horizontally on the operating surface. These positioning devices may remain attached to the operating surface, and encouraging the patient to remain in position, throughout the remainder of the processes of flow 20 according to embodiments.

Figure 14C:
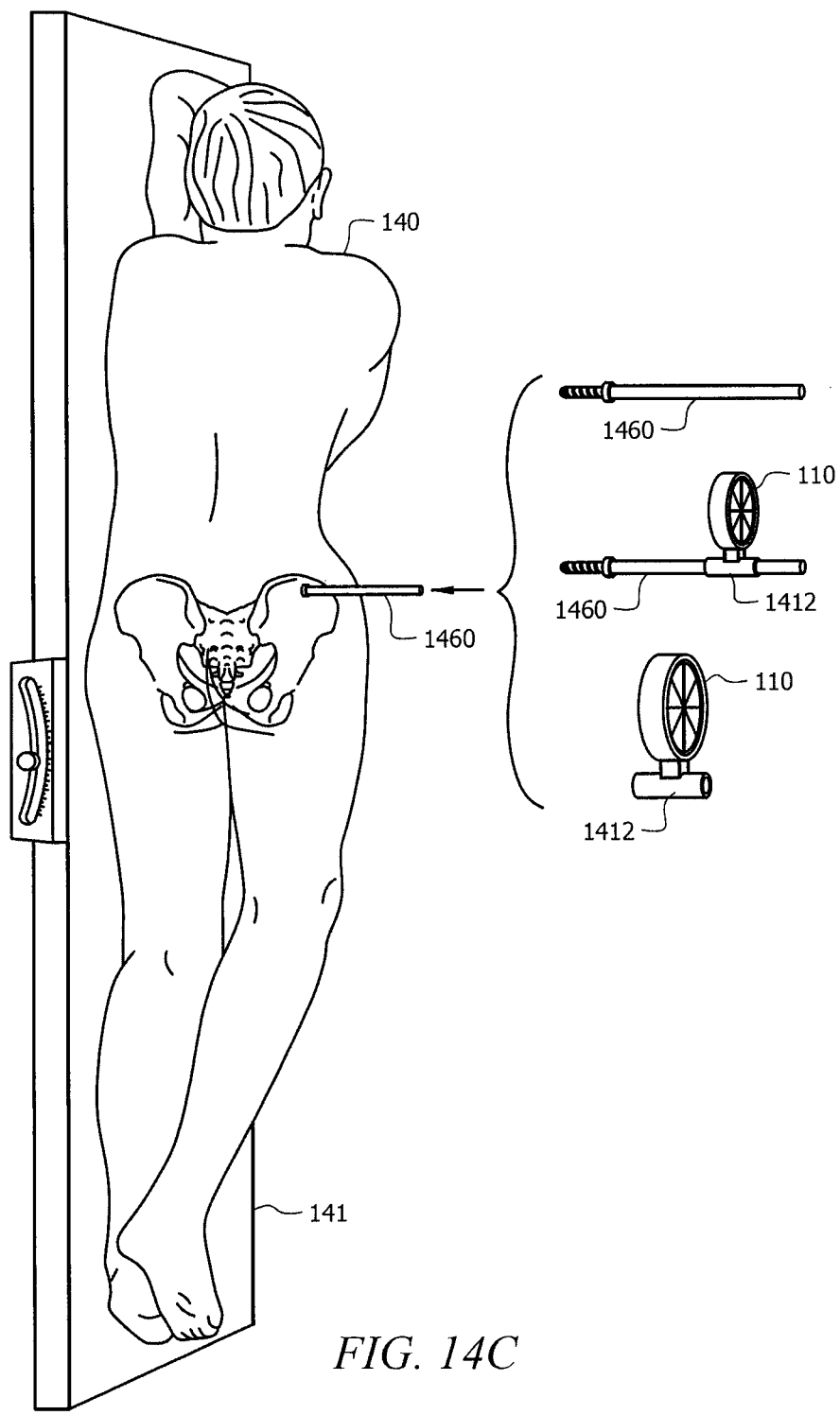
FIGS. 14C-14F show the use of guides according to embodiments of the invention.

A reference guide is placed in the patient in process 203 of the illustrated embodiment. For example, prior to any processes of the implant procedure being performed (e.g., before an incision is made to expose the diseased bones, before dislocation of the hip, etc.) reference guide 1460 may be placed into the patient's pelvic bone (e.g., at the pelvic brim) through a small incision or stab wound as shown in FIG. 14C. In operation according to embodiments of the invention, reference guide 1460 is utilized as a reference to ensure that patient 140 is in a desired position throughout subsequent processes and/or as a positional reference. Thus, reference guide 1460 is preferably placed precisely.

Figure 14D:
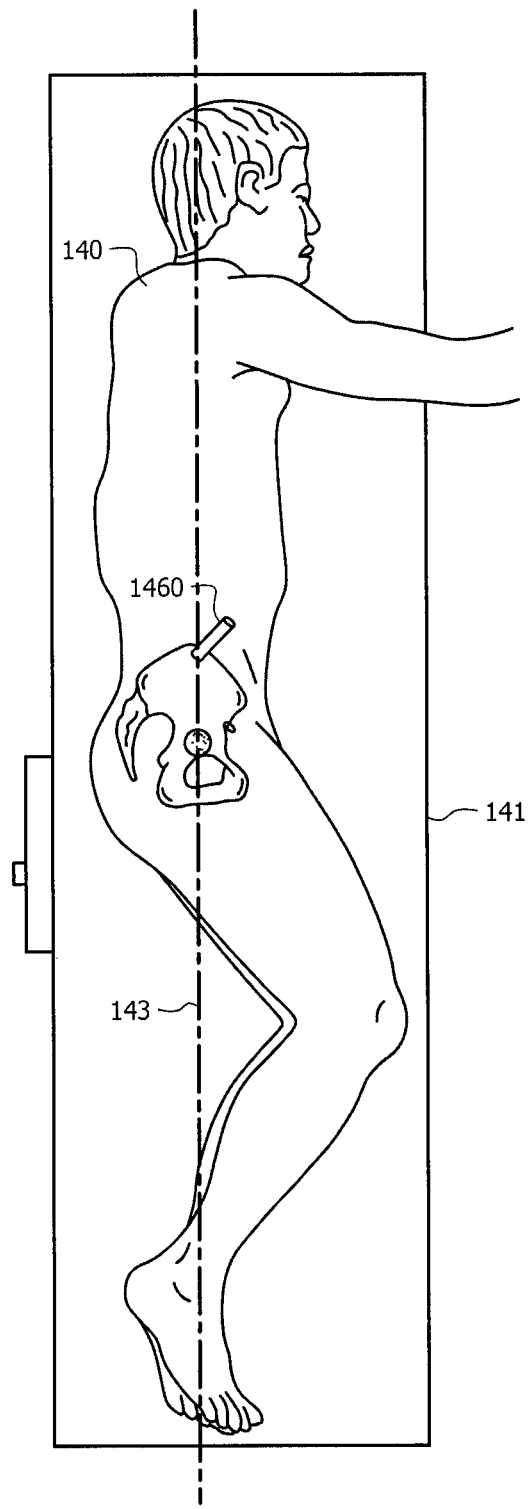

In placing reference guide 1460 according to an embodiment of the invention, a position of the reference guide is selected using one or more techniques, such as review of pre-operation images (e.g., x-ray images, MRI images, ultrasound images, CT images, etc.), palpation to identify subdermal structure and/or features, etc. For example, by studying one or more images of the patient's bone structure and palpating the area, a medical practitioner may identify a desired location for placing reference guide 1460. Such a location may be at an apex of the pelvic brim, on a longitudinal imaginary line extending through the center of the diseased bone or joint being replaced (e.g., the line of coronal plane 143 (an imaginary plane dividing the body into anterior and posterior portions) illustrated in FIG. 14D), or other location useful as a reference point.

Where reference guide 1460 is to be utilized as a reference to ensure the patient has remained in a desired position, reference guide 1460 of embodiments is placed in a predetermined or known orientation. For example, where the operating surface is horizontal and level, reference guide 1460 may be placed in a vertical orientation, orthogonal to the plane of the operating surface. To facilitate placing reference guide 1460 in a desired orientation, embodiments of the invention utilize a visual guide to guide placing the reference guide.

Visual guide 110, such as may comprise a tilt sensing device (e.g., senses angular tilt), is used according to embodiments of the invention to dispose reference guide 1460 in a desired orientation, as shown in FIG. 14C. For example, after identifying the position on the patient for placement of reference guide 1460, visual guide 110 is interfaced with reference guide 1460 to provide a visual indication of orientation of reference guide 1460. For example, a portion of reference guide 1460 is inserted into a tubular housing, preferably having a lumen sized to accept the portion of reference guide 1460 with minimal movement, attached to visual guide 110. Reference guide 1460 may thus be placed into the bone of the patent patient at the identified location in a desired orientation (e.g., vertical, with no tilt) through reference to visual guide 110.

It should be appreciated that visual guide 110 as may be utilized according to embodiments of the invention may comprise any of a number of configurations useful for providing guidance. For example, visual guide 110 of embodiments may comprise one or more of an accelerometer, liquid capacitive, electrolytic, mercury, gas bubble liquid, pendulum and digital sensing device. Embodiments of visual guide 110 may comprise tilt sensing devices operable to measure the angle between a surface and a line or plane that is perpendicular to a line or plane through the earth's center of gravity and/or to measure angular tilt based on an artificial horizontal plane. Accordingly, tilt sensing devices utilized according to embodiments are able to monitor angles in one plane while other tilt sensing devices utilized according to embodiments are able to monitor angles in a plurality of planes. For example, a tilt sensing device of visual guide 110 may be configured to monitor angles in the plane in which the abduction angle is measured, and also to monitor in the plane in which the anteversion angle is measured. Tilt sensors as may be utilized in providing a visual guide according to embodiments of the invention are available from companies such as Microstrain®, and Rieker Incorporated. Further, a description of the operation of these types of devices may be found in U.S. Pat. No. 7,433,798 entitled "SOLID STATE ORIENTATION SENSOR WITH 360 DEGREE MEASUREMENT CAPABILITY," and U.S. Pat. No. 5,953,683 entitled "SOURCELESS ORIENTATION SENSOR," the complete disclosures of which are incorporated herein by reference.

Figure 11A:
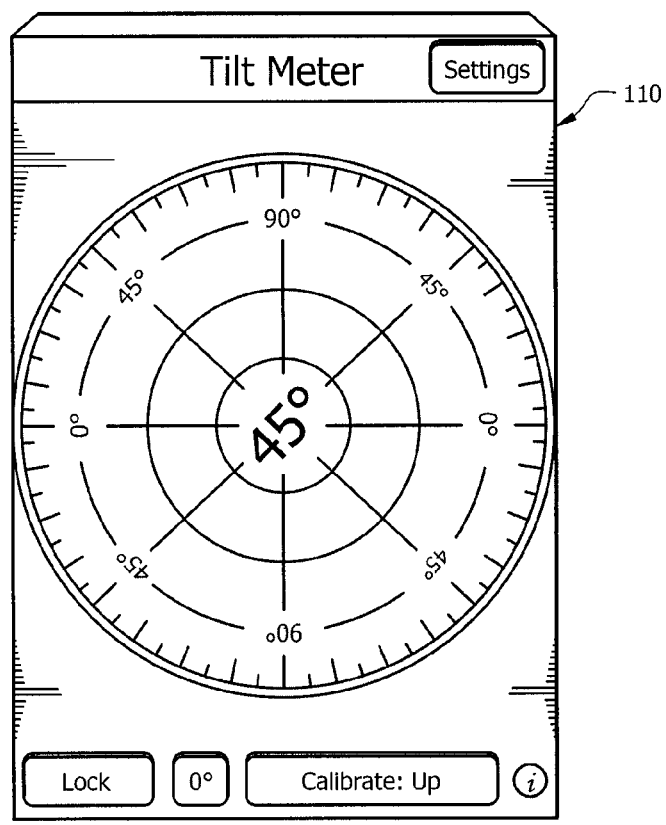
FIGS. 11A-11E show visual guide configurations according to embodiments of the invention.
Figure 11B:
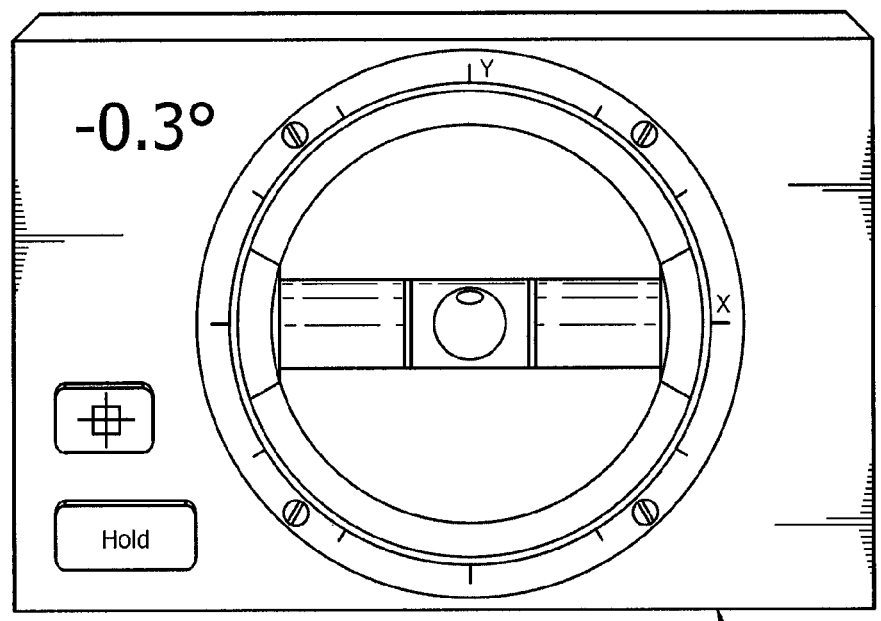
Figure 11C:
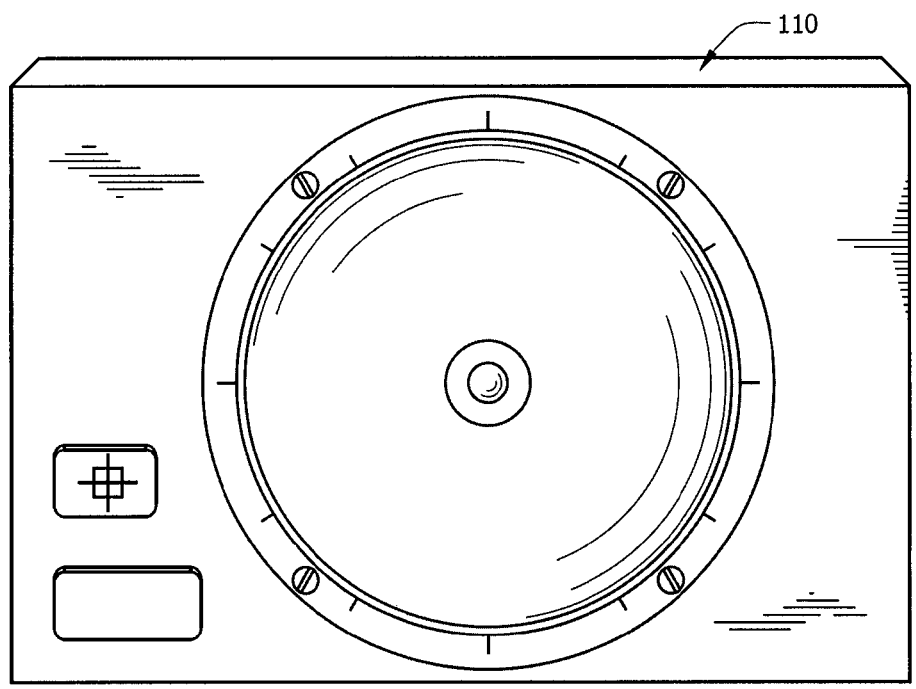
Figure 11D:
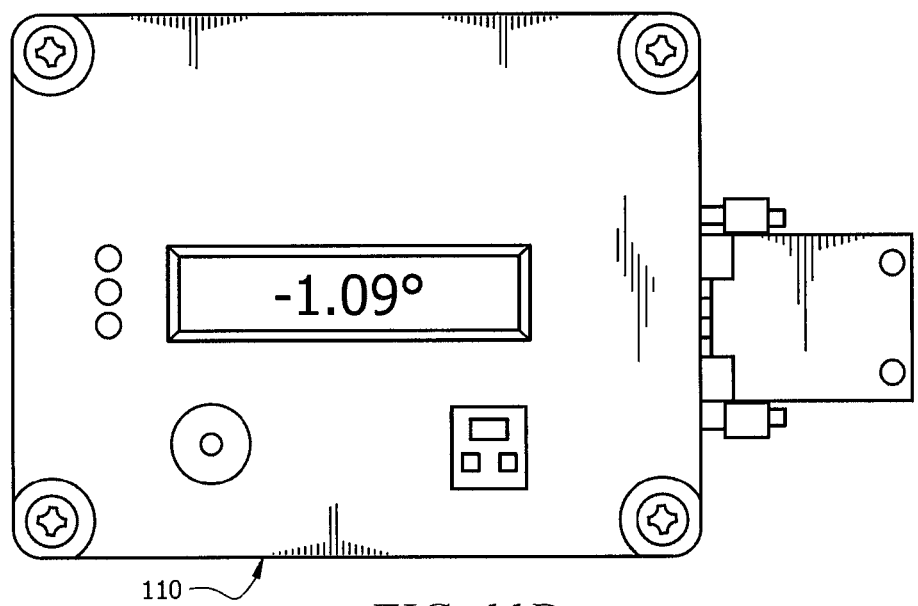
Figure 11E:
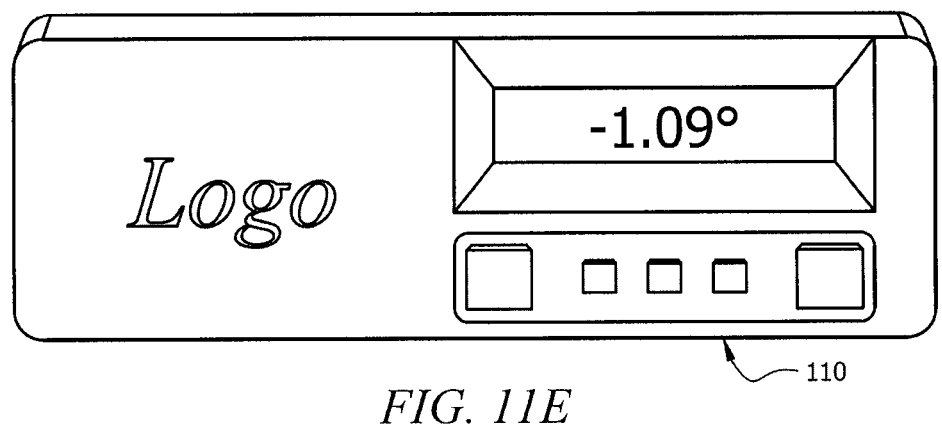

Visual guide 110 may comprise mechanical sensing devices, as shown in FIGS. 11A-11C, electronic sensing devices, as shown in FIGS. 11D-11E, or combinations thereof. Moreover, although visual guide 110 has been described as providing a visual guide, it should be appreciated that visual guides implemented according to embodiments of the invention may provide sensory input in addition to or in the alternative to visual input. For example, audio tones may be provided for guidance, such as to indicate when the desired orientation is achieved and/or when the desired orientation has not been achieved.

Figure 4A:
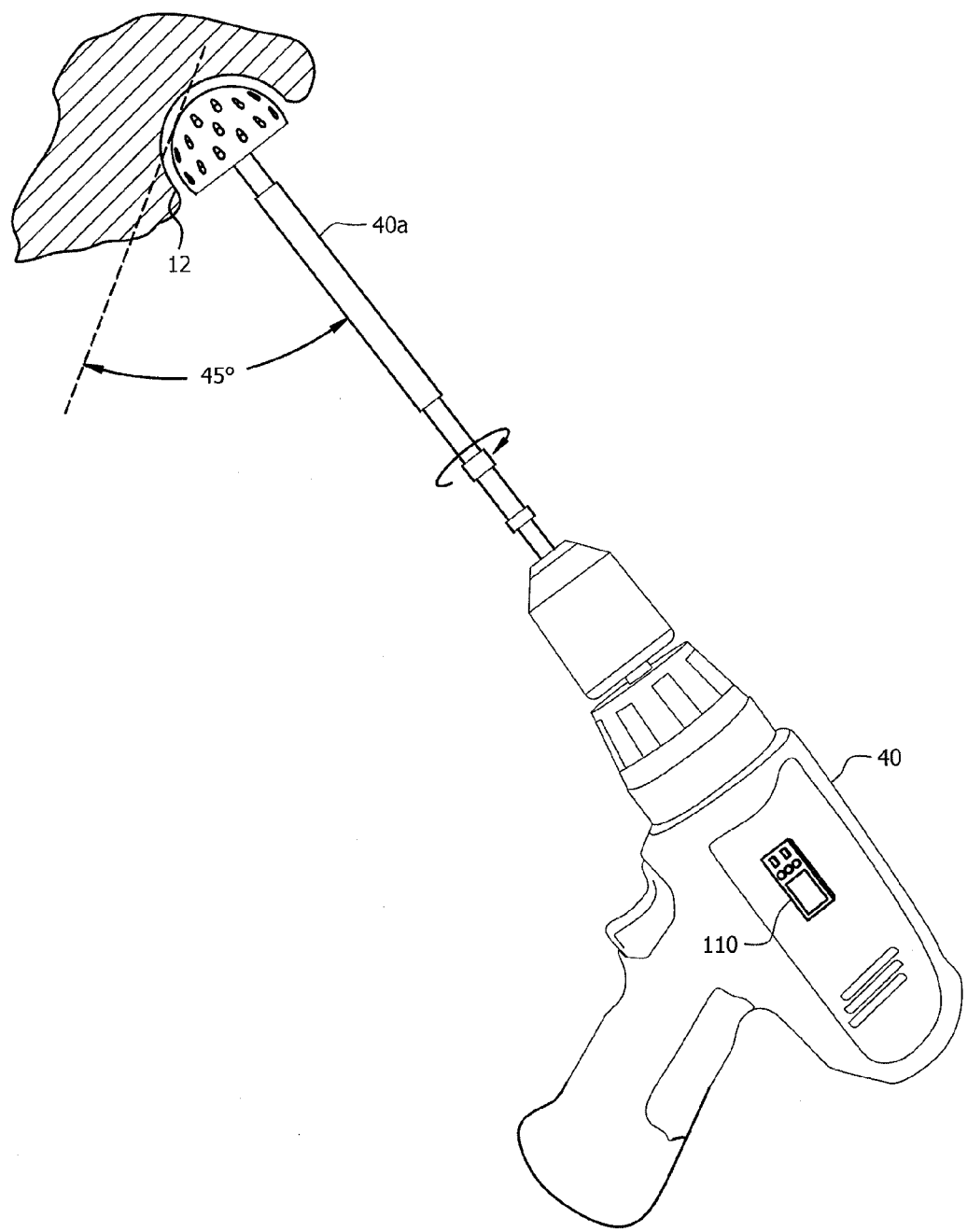
FIG. 4A shows a reamer and drill utilized with respect to a bone cavity according to an embodiment of the invention.
Figure 7A:
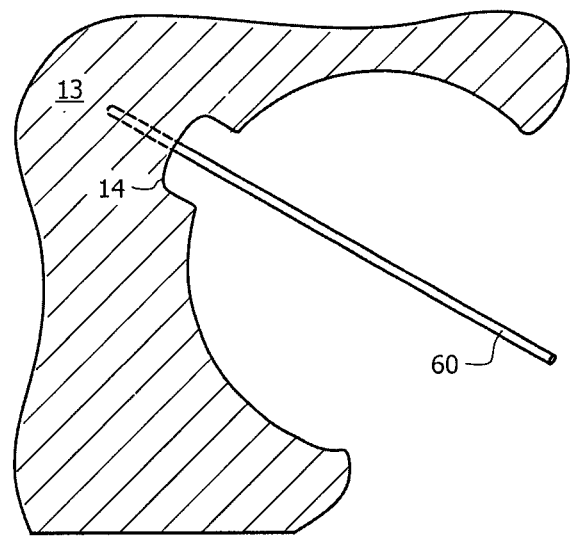
FIGS. 7A-7C show the use of guides to properly align a prosthetic socket in a bone cavity according to embodiments of the invention.
Figure 7B:
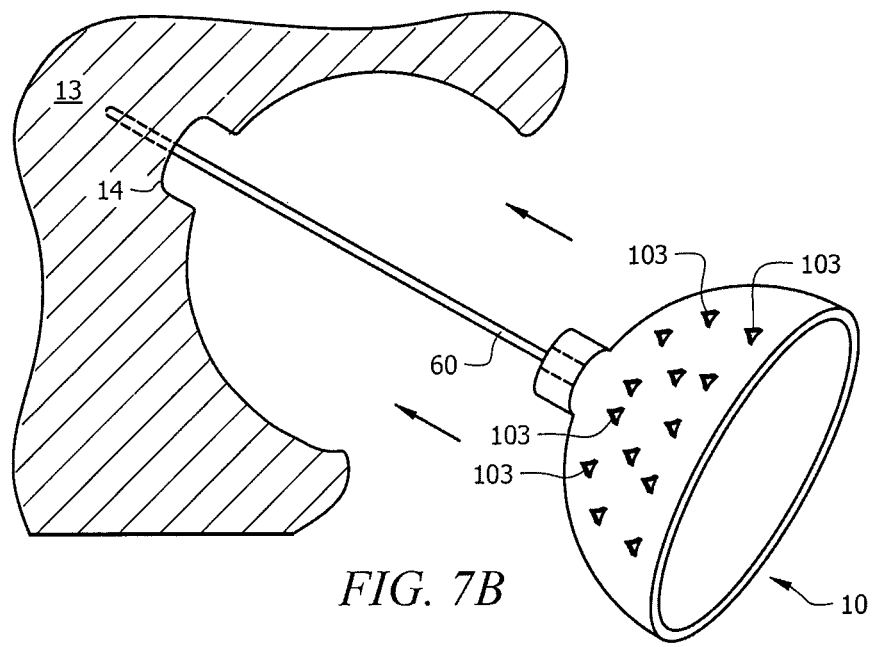
Figure 7C:
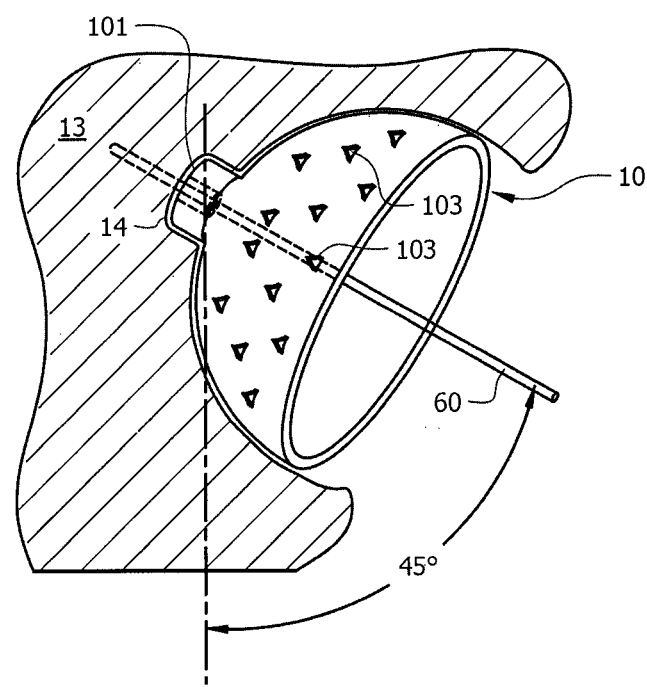

In process 204 of the illustrated embodiment, the bone that forms bone cavity 12 (FIGS. 4A and 4B) into which prosthetic socket 10 (FIGS. 7B and 7C) is to be inserted is prepared by using a reamer to remove unwanted material such as arthritic bone. For example, reamer 40a, as may be provided power drill 40, may be used to remove material within cavity 12 in preparation for receiving prosthetic socket 10 as shown in FIG. 4A. IN operation according to a preferred embodiment, enough material is removed so that bone cavity 12 is deep enough, sized and/or shaped to accept prosthetic socket 10. In order to facilitate placing of prosthetic socket 10 in a desired orientation (e.g., having the desired or proper amount of abduction angle and anteversion angle) one or more guides of the present invention may be utilized with respect to reamer 40a. For example, visual guide 110 may be disposed on drill 40 to provide guidance with respect to operation of reamer 40a to provide a resulting bone cavity adapted to accept prosthetic socket 10 in a desired orientation. Likewise, visual guide 110 may be disposed on reamer 40a, such as upon a shaft portion thereof, to provide the aforementioned guidance.

In process 205 of the illustrated embodiment, trial 30 (FIG. 3) is placed into bone cavity 12. Trial 30 of embodiments has a drill guide channel 301 and a hemispherical shape conforming to the shape of bone cavity 12. Trial 30 is temporarily fitted in a desired position in bone cavity 12 and stabilized with short screws through screw holes 304, which are later removed. This desired position can be determined by various techniques such as manually by a practitioner based on experience, x-ray positioning, fluoroscopy or guidance by other electronic equipment. Additionally or alternatively, in one embodiment, the placing of trial 30 in bone cavity 12 is done under guidance of visual guide 110, such as may comprise a tilt sensing device as discussed above.

In carrying out the hip replacement procedures that utilize the guidance of tilt sensing device as may be provided by visual guide 110, the patient is preferably horizontal and positioned consistent with the planes used as the basis for the particular angle being measured. Reference to reference guide 1460 may be utilized to confirm that the patient is disposed in the desired position as initially provided in process 202 discussed above. For example, visual guide 110 may be utilized with respect to reference guide 1460 to confirm that the patient remains in the desired position and/or to correct the patient's position to remediate any movement that may have occurred.

Figure 13:
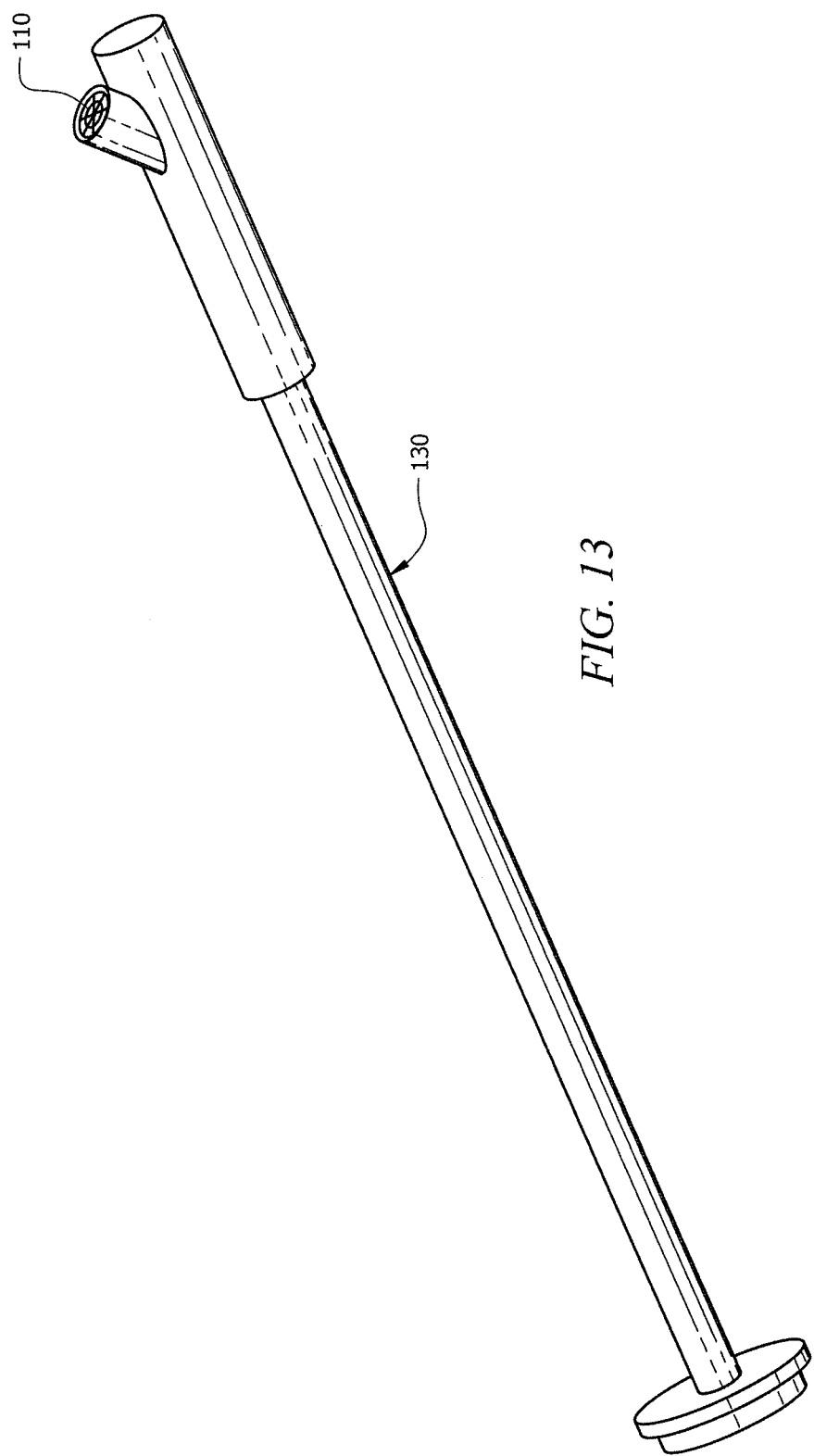
FIG. 13 shows a positioner/driver device having a visual guide disposed thereon according to an embodiment of the invention.
Figure 14E:
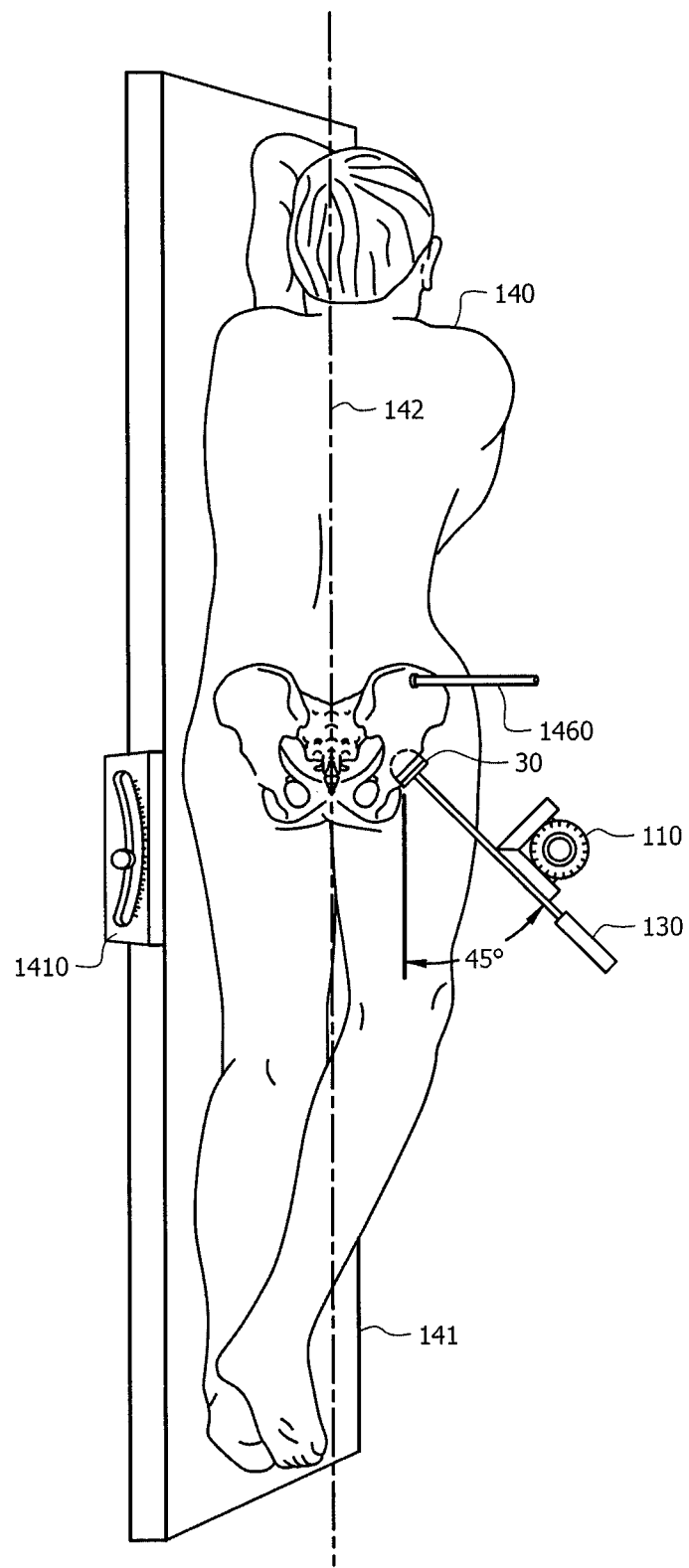
Figure 14F:
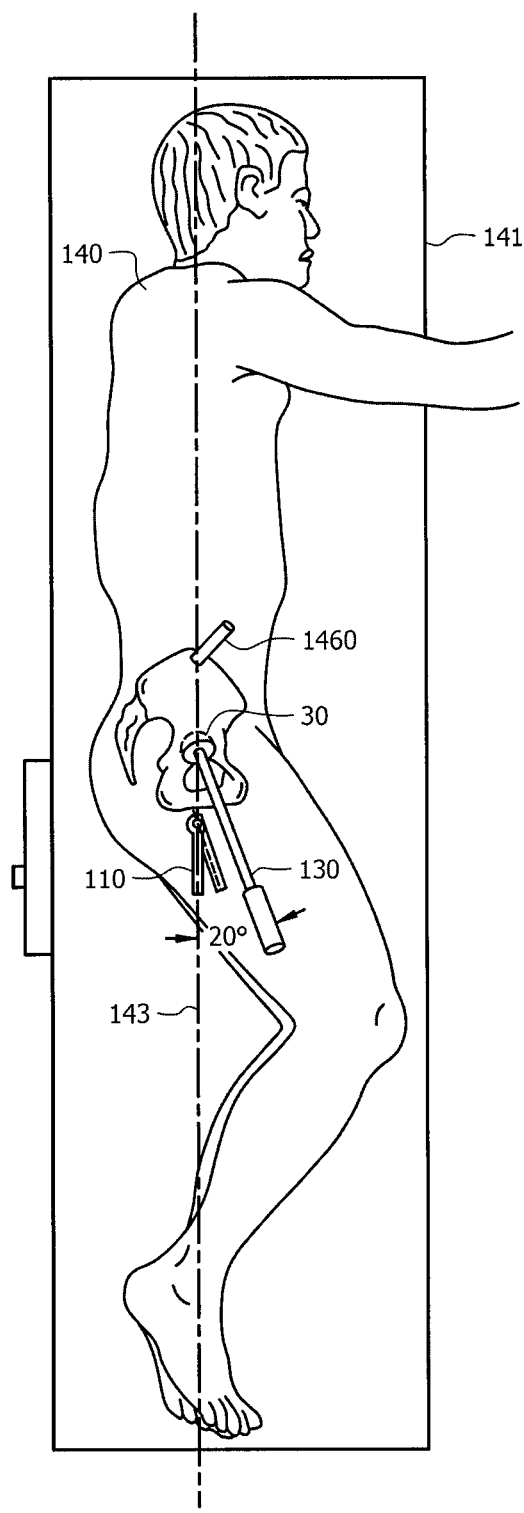

FIG. 13 shows positioner/driver device 130 that is adapted to be used to position trial 30 or drive prosthetic socket 10 into the hip of patient 140. FIGS. 14E and 14F illustrate trial 30 being positioned in the hip of patient 140 using guides according to embodiments of the invention. FIG. 14E shows the measurement of the abduction angle by visual guide 110 which is attached to positioner/driver device 130. FIG. 14F shows the measurement of the anteversion angle using visual guide 110 according to embodiments.

As illustrated in FIGS. 14E and 14F, operating surface 141 is horizontal with patient 140 is on his or her side on operating surface 141. As such, sagittal plane 142 (an imaginary plane that divides the body into right and left sections) is parallel to operating surface 141. Therefore, the abduction angle of positioner/driver device 130 is the angle between positioner/driver device 130 and sagittal plane 142 as shown in FIG. 14E. The anteversion angle of visual guide 110 is the angle between coronal plane 143 (an imaginary plane dividing the body into anterior and posterior portions) and positioner/driver device 130 as shown in FIG. 14B. It should be noted that coronal plane 143 and sagittal plane 142 are perpendicular to each other. To measure the abduction angle, a tilt sensing device of visual guide 110 should be calibrated/synchronized to measure 0° for sagittal plane 142 according to embodiments. Similarly, to measure the anteversion angle, a tilt sensing device of visual guide 110 may be calibrated/synchronized to measure 0° for coronal plane 143.

Embodiments of the invention utilize reference guide 1460 in combination with visual guide 110 for measurement of the anteversion angle. For example, visual guide 110 may comprise a goniometer device (e.g., protractor type device) from which the anteversion angle is determined. Reference guide 1460 may be utilized as a reference point establishing an imaginary line (e.g., the line of coronal plane 143 shown in FIG. 14F) from which a goniometer device of visual guide 110 measures the anteversion angle, as shown in FIG. 14F.

Figure 3E:
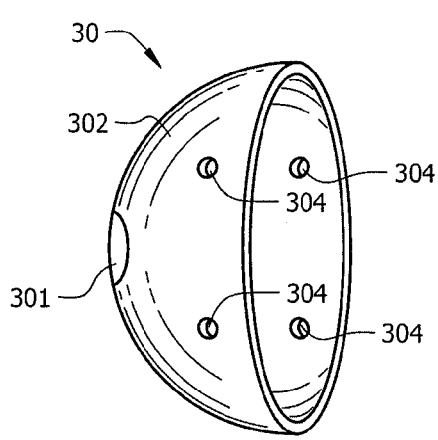
Figure 3E:
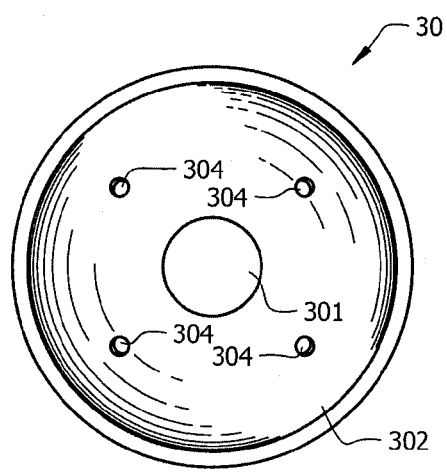
Figure 3E:
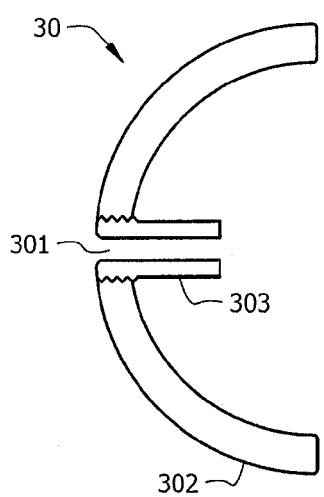
Figure 3E:
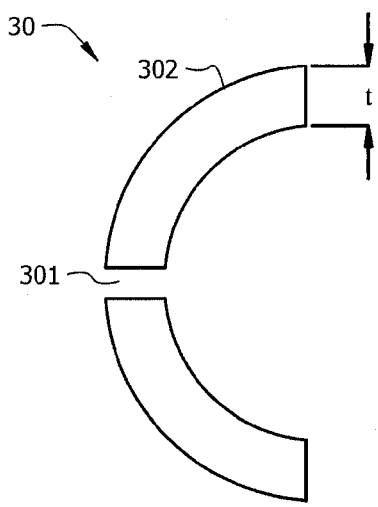
Figure 3E:
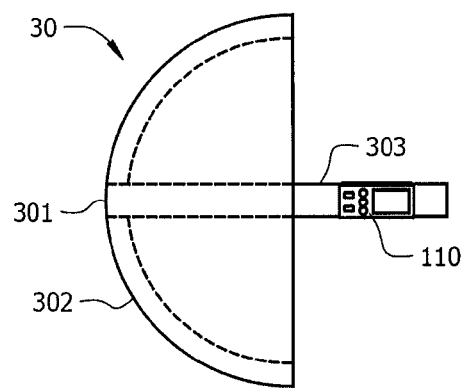

Guides of embodiments of the invention may be disposed on or more directly on trial 30 and/or prosthetic socket 10, if desired. For example, in one embodiment, visual guide 110 may be attached to extended drill guide channel 303 of trial 30 as shown in FIG. 3E. Drill guide channel 303 may be removed from dome 302 after trial 30 is properly positioned in bone cavity 12.

In performing process 205 of embodiments, a trial reduction may be performed with respect to trial 30. Trial reduction involves placing and maneuvering a prosthetic ball in the fitted trial to check for proper alignment, stability and range of motion. Accordingly, in some embodiments of the invention, a liner may be placed in trial 30 and a trial reduction performed.

Figure 4B:
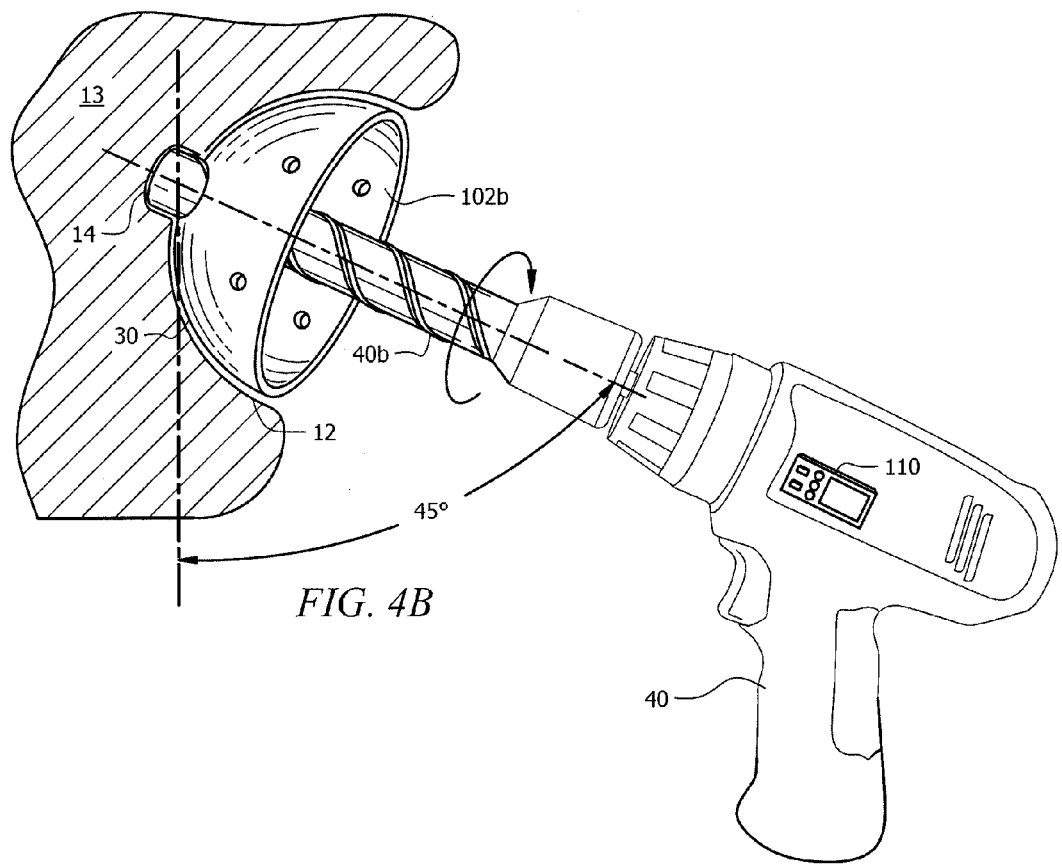
FIG. 4B show a trial and drill in a bone cavity according to an embodiment of the invention.

Once trial 30 is in the desired position, in process 206 of the illustrated embodiment a peg positioning bore is drilled into the bone that forms the bone cavity into which the prosthetic socket is to be placed. For example, peg positioning bore 14 may be drilled into bone 13 by placing drill bit 40b through drill guide channel 301 of trial 30, as shown in FIG. 4B. Peg positioning bore 14 is drilled into the bone to about one centimeter past dome 302 according to embodiments of the invention.

It should be noted that drill guide channel 301 has a channel that guides or channels drill bit 40b to precisely correspond with the alignment of trial 30. Additionally, drill 40 may be fitted with visual guide 110 to ensure the proper angle corresponding to the alignment of trial 30 is maintained at all times during the drilling. Thus, drill guide channel 301 and visual guide 110 define the angle in which peg positioning bore 14 is being drilled by drill bit 40b.

Drill guide channel 301 defines the angle of peg positioning bore 14 by being only slightly larger in diameter than drill bit 40b so that drill bit 40b can enter the bone in one direction only. In some embodiments, drill bit 40b could have a much smaller diameter than drill guide channel 301. In such an embodiment, an appropriately sized bushing (to make up for the small diameter of drill bit 40b) could be placed on drill bit 40b and this bushing in conjunction with drill guide channel 301 would provide the proper alignment of drill bit 40b.

Apart from the diameter of (1) drill guide channel 301, or (2) drill guide channel 301 in conjunction with a properly sized bushing, a sufficient thickness "t" (FIG. 3D) of dome 302 may help to ensure drill bit 40b does not have any "room to play" and can enter bone 13 in one direction only, as long as it is in drill guide channel 301. Alternatively, removable extension 303, which forms drill guide channel 301, may also be used to guide drill bit 40b at a specific angle into bone 13. Removable extension 303 may be connected to dome 302 by, for example, a screw and tapped hole mechanism.

Figure 5:
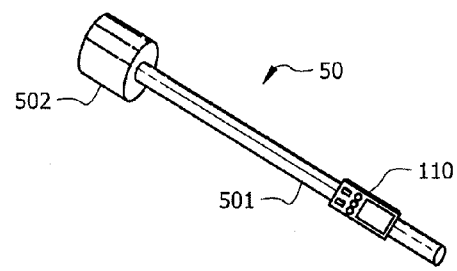
FIG. 5 shows a physical guide according to an embodiment of the invention.
Figure 6:
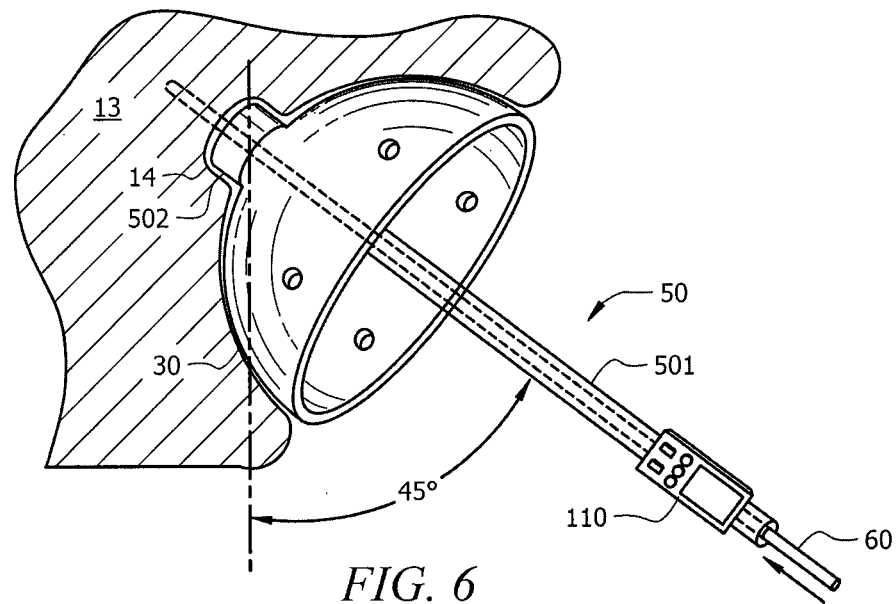
FIG. 6 shows the insertion of a guide piece into bone under guidance of a physical guide according to an embodiment of the invention.

In process 207 of the illustrated embodiment, physical guide 50 (FIG. 5) is placed into peg positioning bore 14. Physical guide 50 of the embodiment illustrated in FIG. 5 comprises a drill guide having a cannulated cylinder 501 and a cannulated sleeve 502. Cannulated cylinder 501 and cannulated sleeve 502 have lumens sized to accommodate physical guide 60 (FIG. 6). Sleeve 502 is slightly larger than drill bit 40b and therefore fits tightly into the peg positioning bore 14 at the same angle drill bit 40b entered bone 13 under guidance of trial 30. Additionally, the placing of physical guide 50 may be done under guidance of visual guide 110 attached to physical guide 50.

As shown in FIG. 6, physical guide 50 of embodiments is used as a guide to insert physical guide 60 into bone 13, in process 208. Physical guide 60 may comprise a Kirschner wire or other appropriate wire, pin rod etc. for providing physical guidance as described herein. In operation according to embodiments of the invention, physical guide 60 may be drilled or pushed into bone 13, such as to a depth of about one centimeter into bone 13.

Because physical guide 50 is located in bone 13 in a position and alignment according to the position and alignment of trial 30 and the lumen of physical guide 50 precisely guides physical guide 60 into bone 13, physical guide 60 of embodiments is inserted in bone 13 according to the position and alignment of trial 30. That is, because physical guide 50 is used to guide physical guide 60 into bone 13, physical guide 60 enters bone 13 at the same position and direction as drill bit 40b did. As such, physical guide 60 is an indicator of the position of trial 30 when trial 30 was fitted in bone cavity 12. Moreover, in embodiments that include visual guide 110, visual guide 110 may be used to ensure that proper position and alignment of physical guide 50 is maintained throughout the procedure. In another embodiment of the invention, instead of placing physical guide 50 into peg positioning bore 14, physical guide 50 is placed in drill guide channel 301 while providing guidance for the insertion of physical guide 60 into bone 13.

In process 209 of the illustrated embodiment, physical guide 50 and trial 30 are removed from bone cavity 12 leaving physical guide 60. Thus in process 210, prosthetic socket 10 is positioned, in the same position and angle as the trial was, using physical guide 60 for guidance. For example, in operation according to embodiments, prosthetic socket 10 is placed over the physical guide 60 so that physical guide 60 fits into lumen 101a of peg 101. Prosthetic socket 10 is then slid along physical guide 60 into bone cavity 12. Peg 101, which has a slightly larger diameter than drill bit 40b (and thus peg positioning bore 14), is positioned in peg positioning bore 14 prior to more secure fastening to bone 13.

Process 211 of the illustrated embodiment provides for securing prosthetic socket 10 to bone 13, as illustrated in FIGS. 8A and 8B. This is done according to embodiments by using physical guide 80. Physical guide 80 of embodiments, such as may comprise a prosthetic socket driver, has aperture 80a in it that allows physical guide 80 to fit over physical guide 60 as physical guide 80 is used to tap prosthetic socket 10 in place. Additionally, physical guide 80 may comprise a visual guide 110. Thus, visual guide 110 attached to physical guide 80 may be used to guide the process of driving prosthetic socket 10 in at the correct angle.

Prosthetic socket 10 is tapped in place to loosely engage bone 13 in the desired position according to embodiments of the invention. Physical guide 60 is then removed providing more room for prosthetic socket 10 to be more forcefully driven in place by physical guide 80. Here, visual guide 110 attached to physical guide 80 continues to provide guidance for the driving process in the absence of physical guide 60. In another embodiment of the invention physical guide 60 may be kept in place in bone 13 to guide the forceful driving of prosthetic socket 10 in place by physical guide 80. After prosthetic 10 is securely in place, in this latter embodiment, physical guide 60 is removed.

Figure 9:
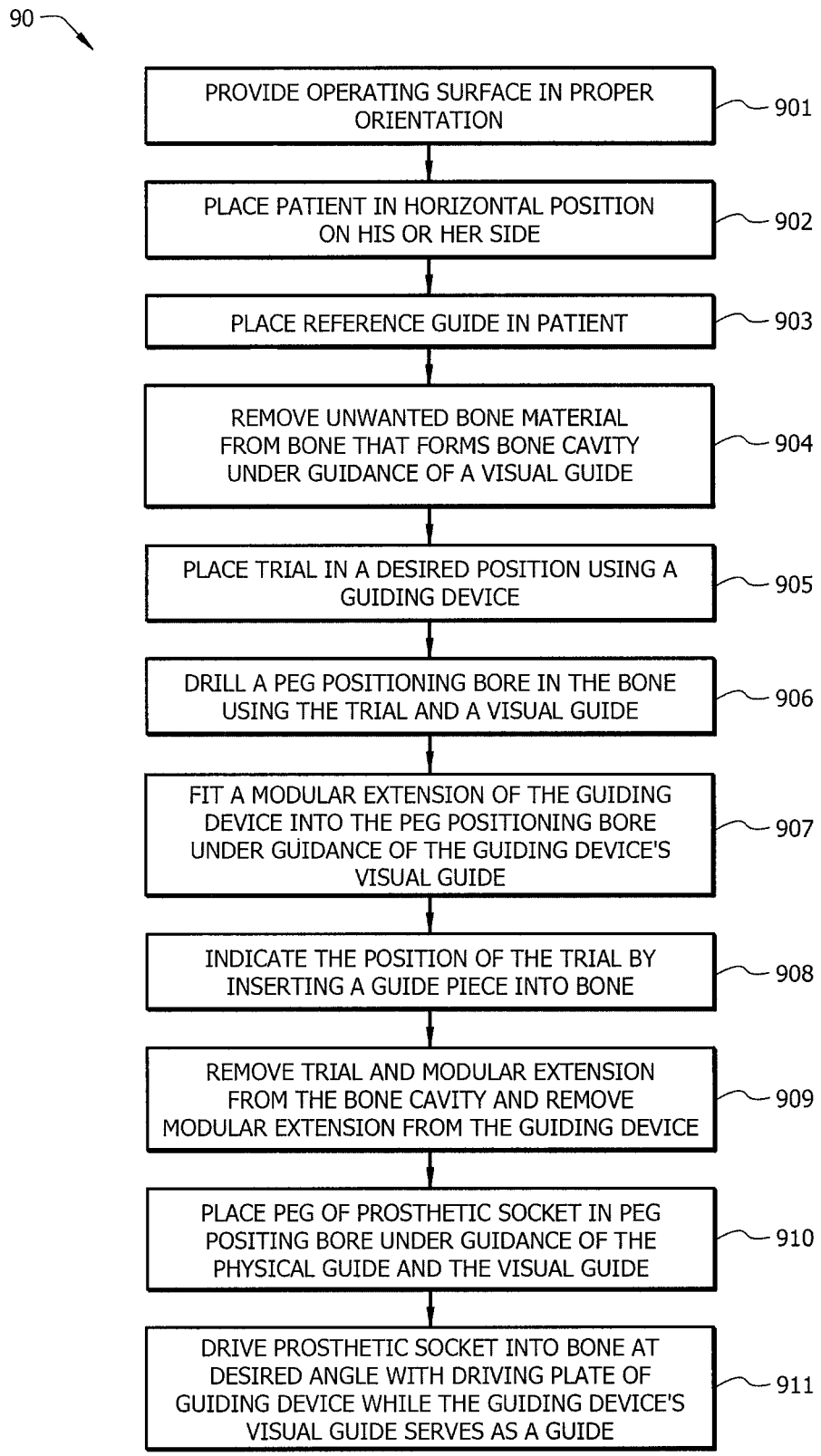
FIG. 9 shows a process to properly align a prosthetic socket using guides according to embodiments of the invention.

FIG. 9 shows flow 90 of other embodiments of the invention that properly fit a prosthetic socket within the bone cavity of a patient. As with the embodiments described with respect to FIG. 2 above, an expected orientation of the prosthetic socket in the patient's bone cavity may be determined in pre-operative analysis. For example, pre-operation images of the patient may be studied to determine the abduction angle and the anteversion angle the prosthetic socket is expected to be disposed in. The desired abduction and antevsion angles of the prosthetic socket may be determined and maintained as a trial and/or the prosthetic socket is being placed in the patient using one or more guides of the present invention. It should be appreciated that the expected abduction and anteversion angles may be modified during an prosthetic implant procedure, such as by placing a trial in a desired position and determining its abduction and anteversion angles using one or more guides herein.

In process 901 of flow 90 of the illustrated embodiment, the operating surface upon which a patient is to be disposed during the prosthetic socket implant procedure is placed in, or confirmed to be disposed in, a proper orientation. For example, to ensure the patient is horizontal, the examination or operating table and floor should be horizontal and level (e.g., the plane of the surface thereof providing a horizontal surface with no tilt). Accurately disposing the patient in a horizontal position is desired according to embodiments in order to establish a proper baseline reference guide, to facilitate use of various visual guides, etc. The operating table or other surface may be provided with a position guide, such as level 1410 shown in FIG. 14B, for use in placed in a proper or desired orientation.

In process 902 of the illustrated embodiment, patient 140 is positioned horizontally on his or her side as described in process 202 of flow 20 above. Positioning devices, such as positioning devices 1401 shown in FIGS. 14A and 14B, may be utilized to encourage a patient to remain in a desired position during all or some part of the procedure.

A reference guide is placed in the patient in process 903 of the illustrated embodiment. For example, prior to any processes of the implant procedure being performed, reference guide 1460 may be placed into the patient as discussed above with respect to process 203 of flow 20. Reference guide 1460 of embodiments is utilized as a reference to ensure that patient 140 is in a desired position throughout subsequent processes and/or as a positional reference and is thus preferably placed precisely. Techniques for the placement of reference guide 1460 are discussed above with reference to process 203 of flow 20.

Figure 10A:
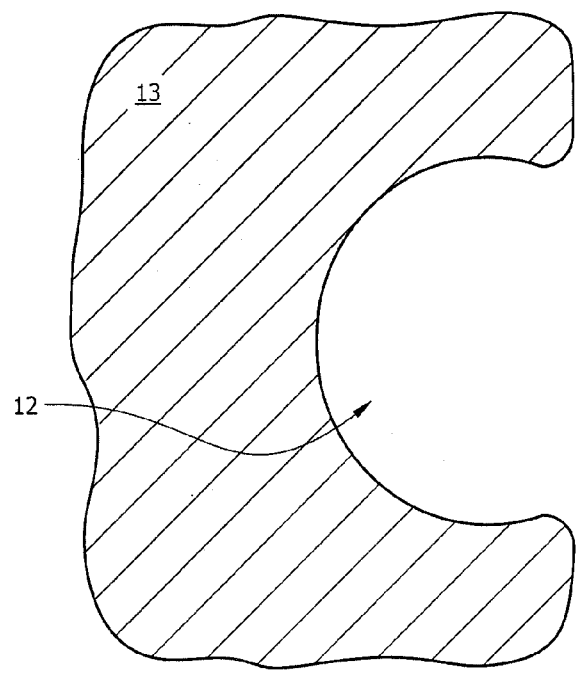

In process 904 of the illustrated embodiment, the natural bone socket is prepared for receiving prosthetic socket 10. As described above with respect to process 204 of flow 20, this includes removal of bone so that bone cavity 12 (FIG. 10A) is sized and shaped to receive prosthetic socket 10, to remove diseased material (e.g., arthritic material), etc. Accordingly reamer 40a (FIG. 4A), as may be provided power by drill 40, may be used to remove material within bone cavity 12. In order to facilitate placing of prosthetic socket 10 in a desired orientation, one or more guides (e.g., a visual guide, a physical guide, and/or a reference guide) of the present invention may be utilized with respect to reamer 40a. For example, visual guide 110 may be disposed on drill 40 or upon reamer 40a to provide guidance with respect to operation of reamer 40a.

Figure 10B:
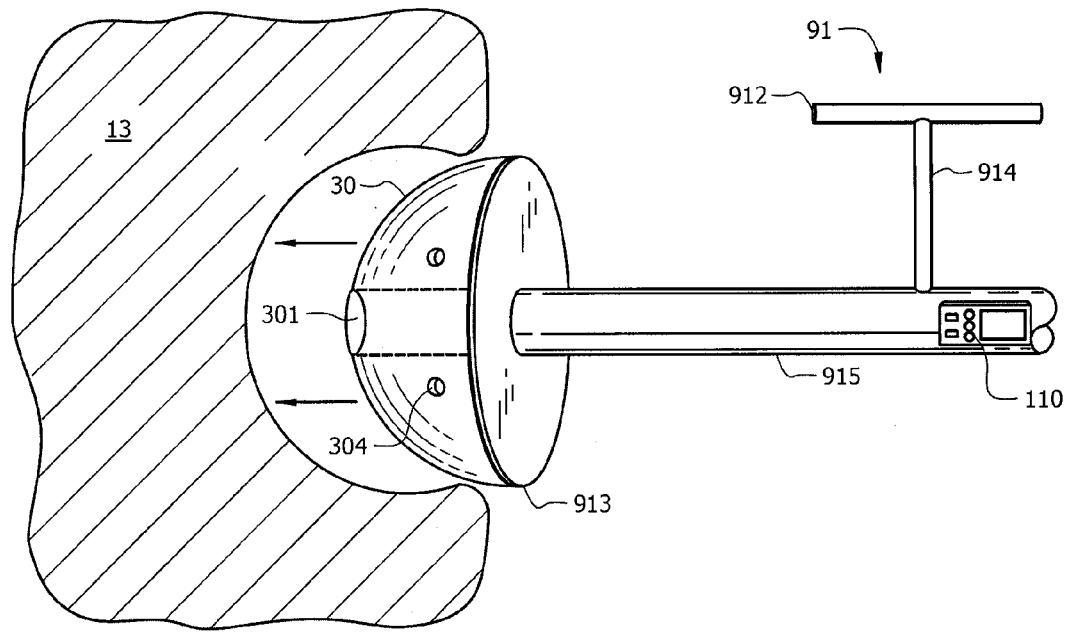

In process 905 of the illustrated embodiment, trial 30 (FIG. 10B) is placed into bone cavity 12 in a desired position. The fitting of trial 30 according to embodiments of the invention utilizes one or more guides herein. For example, fitting of trial 30 according to embodiments of the invention utilizes physical guide 91 and visual guide 110. To fit trial 30 using physical guide 91, modular extension 911 (FIG. 10D), which is sized to fit in guide channel 301 (FIG. 10B), is inserted in guide channel 301. Then modular extension 911, with trial 30 positioned on it, is placed in bone cavity 12 while tilt sensing device 110 indicates a desired abduction and/or anteversion angle as shown in FIG. 10B. Reference guide 1460 may be referenced during the procedure to confirm that patient 140 remains in a desired position for this process. Once placed in the desired position, trial 30 is preferably stabilized by temporarily screwing it in place through screw holes 304.

Figure 10C:
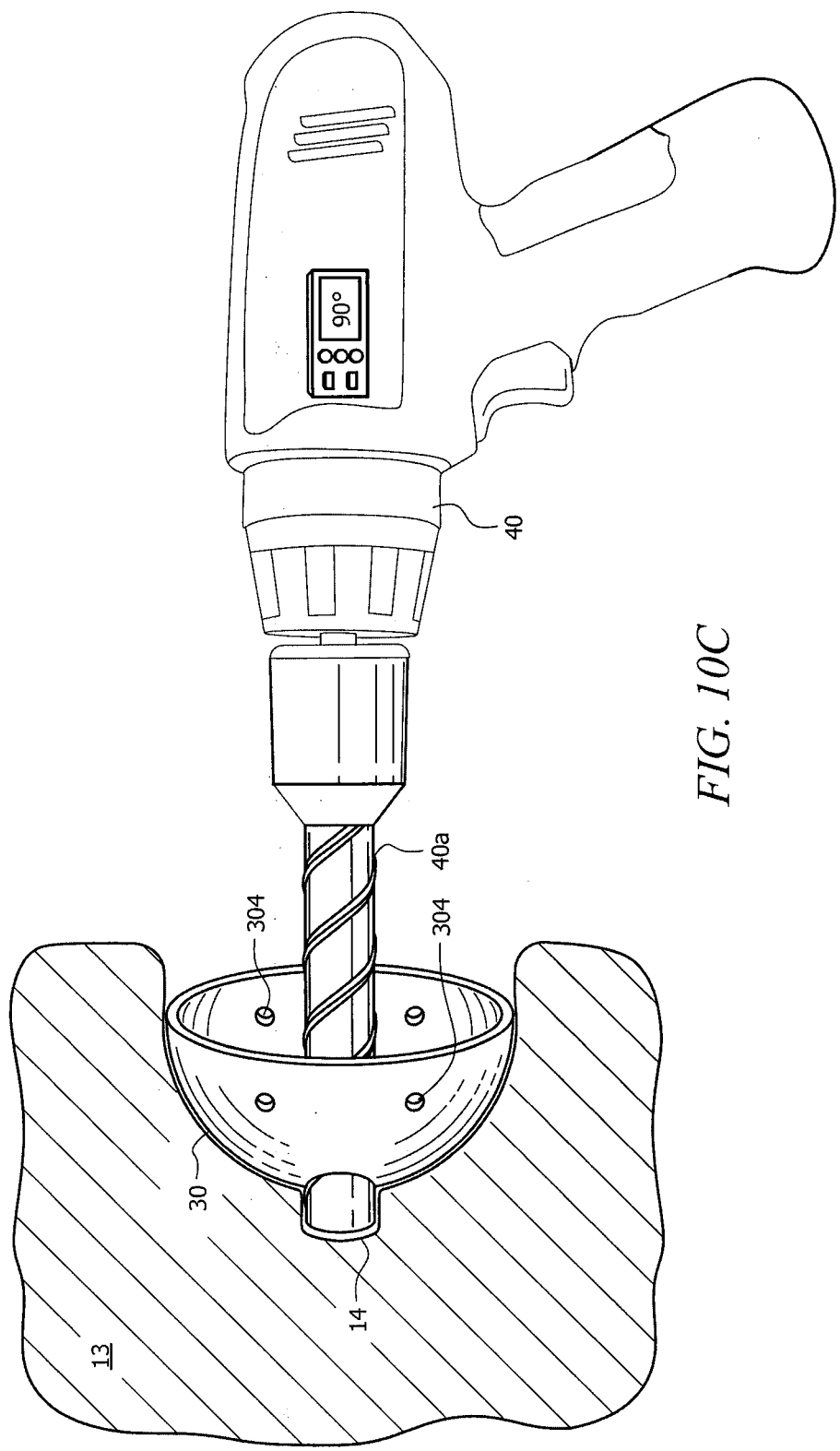

Once trial 30 is stabilized in the desired position, in process 906 of the illustrated embodiment a peg positioning bore is drilled into the bone that forms the bone cavity into which the prosthetic socket is to be placed. For example, peg positioning bore 14 may be drilled into bone 13 by placing drill bit 40b through drill guide channel 301 of trial 30 as shown in FIG. 10C. Drill guide channel 301, as discussed earlier, defines the angle in which drill bit 40b enters bone 13. In other words, trial 30 guides drill bit 40b into bone 13 at a particular angle. Additionally, drill 40 may comprise a visual guide (e.g., visual guide 110) for use in ensuring that drill bit 40b drills peg positioning bore at the correct angle into bone 13.

Figure 10D:
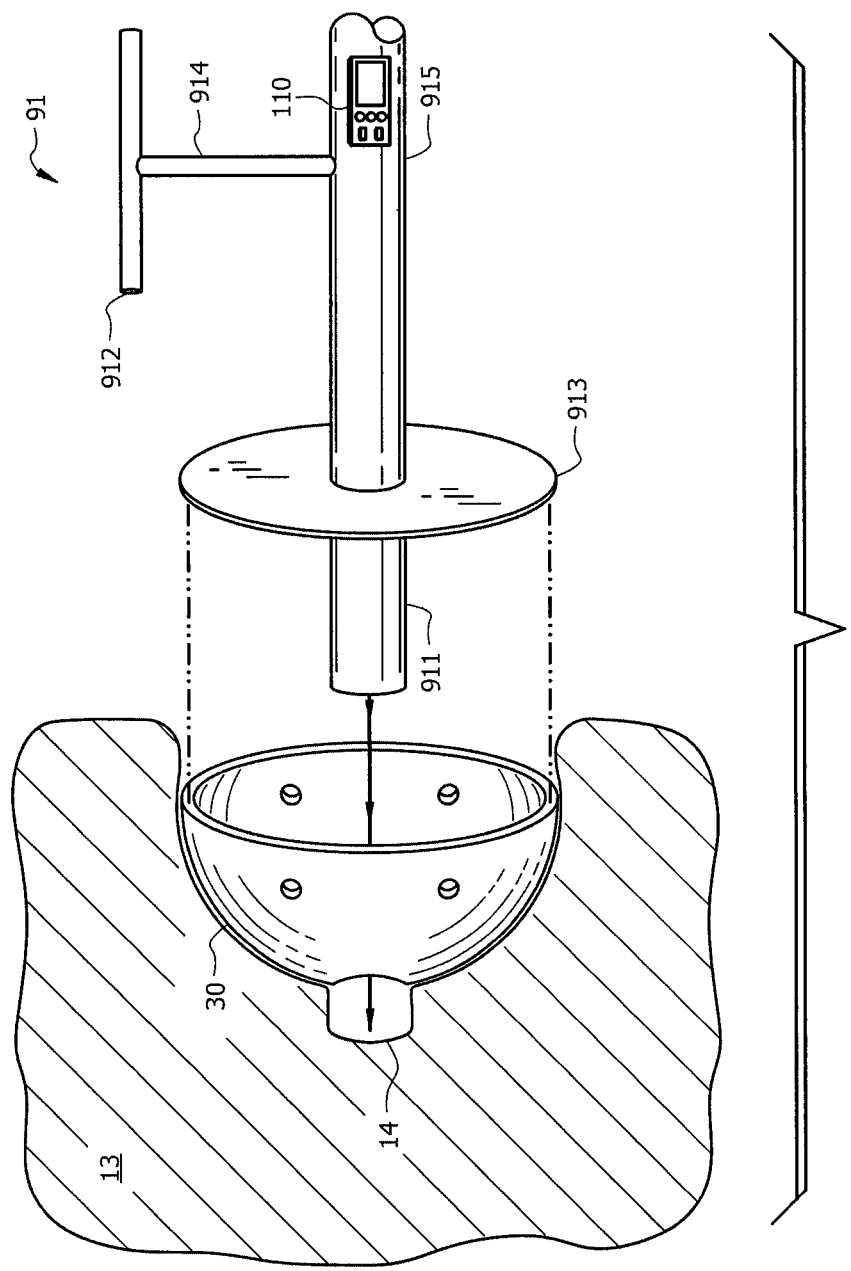
Figure 10E:
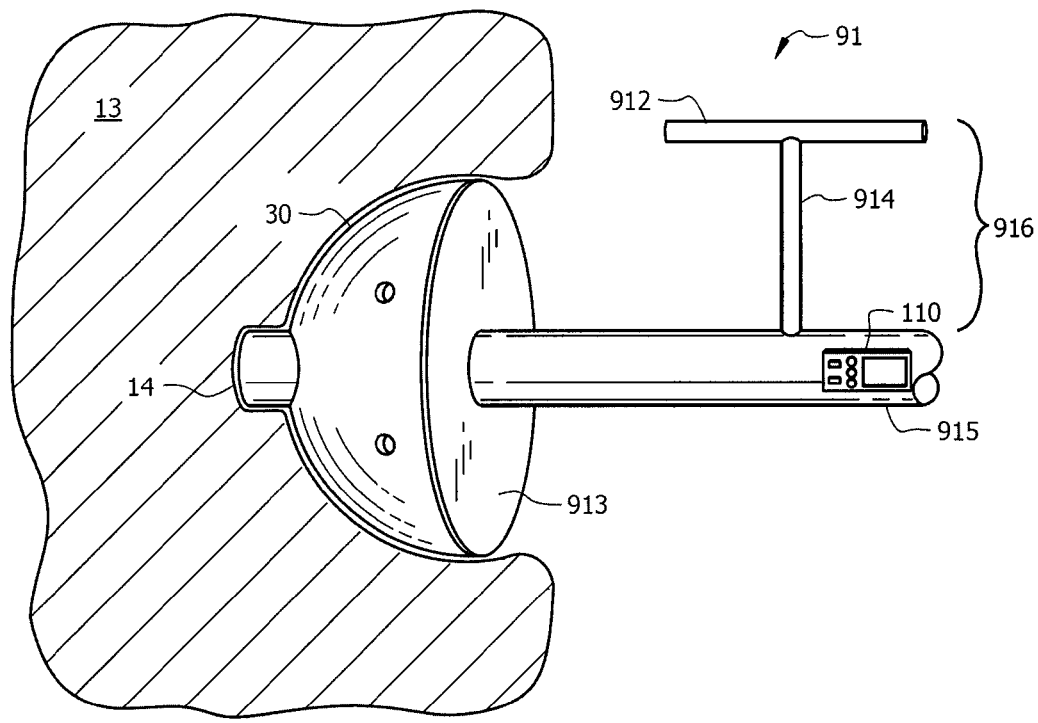

In process 907 of the illustrated embodiment, drill bit 40b is removed and modular extension 911 of physical guide 91 is inserted into peg positioning bore 14 as illustrated in FIGS. 10D and 10E. Visual guide 110 of physical guide 91 is used according to embodiments to guide the insertion of modular extension 911 into peg positioning bore 14 at the desired angle. Physical guide 91 of one embodiment is used to properly fit prosthetic sockets into bone cavities and thus may include a driving plate 913.

Physical guide 91 of embodiments comprises tubular pin guide 912 fixedly attached to portion 915 by connector 914. Tubular pin guide 912 and connector 914 form guide tower 916. Modular extension 911 is removably attached to portion 915. As such, for any direction in which modular extension 911 is pointed, tubular pin guide 912 will point in the corresponding direction. Thus, with modular extension 911 positioned in peg positioning bore 14, which is at the same angle as drill bit 40b entered bone 13, this position and angle are indicated by tubular pin guide 912 of physical guide 91.

Figure 10F:
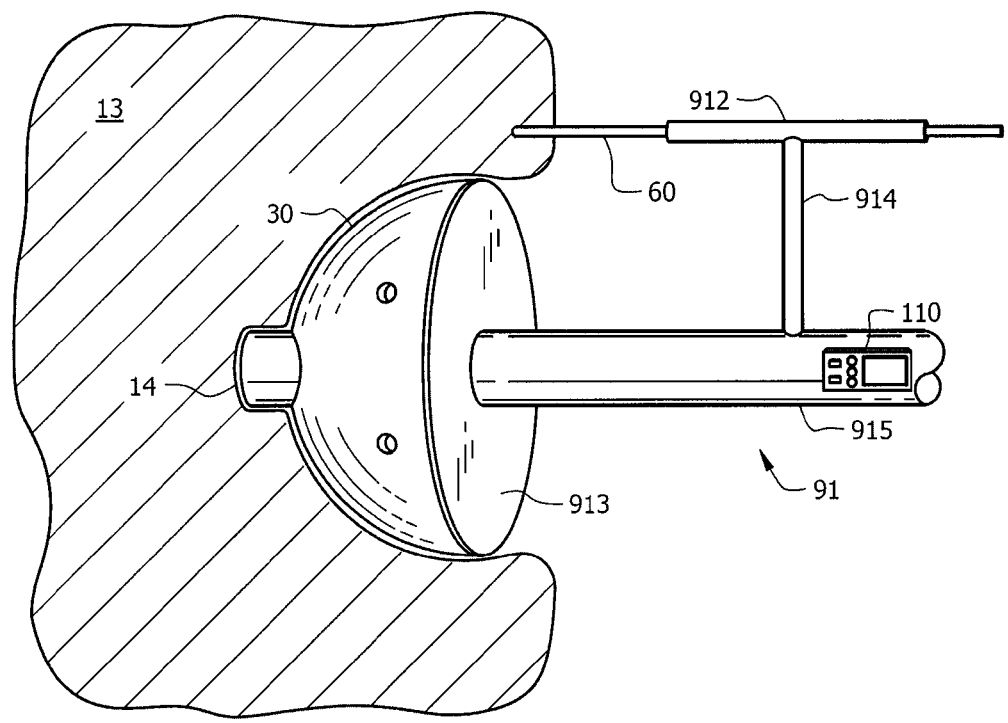

In process 908 of the illustrated embodiment, a corresponding guide piece (shown in FIG. 10F as physical guide 60) is inserted through tubular pin guide 912 of physical guide 91 into bone 13. For example, physical guide 60 may comprise a Steinman pin which is placed into bone 13 near bone cavity 12 under guidance of tubular pin guide 912 so as to indicate the position and angle of trial 30 as shown in FIG. 10F. That is, driving plate 913 rests on the face of trial 30 and the angle in which physical guide 60 is placed into bone 13 is defined by tubular pin guide 912 because the lumen of tubular pin guide 912 is precisely sized to guide physical guide 60 in a particular direction when physical guide 60 is placed in the lumen of tubular pin guide 912. In turn, the position of tubular pin guide 912 is determined by the angle modular extension 911 is set into peg positioning bore 14. Additionally, visual guide 110 disposed upon physical guide 91 of embodiments is used to ensure the proper positioning and alignment of physical guide 91.

In process 909 of the illustrated embodiment, trial 30 is removed from bone cavity 12. Physical guide 91 is also removed from bone cavity 12 and modular extension 911 removed from physical guide 91. However, physical guide 60 preferably remains positioned in bone 13. Using physical guide 60 in conjunction with physical guide 91 as shown in FIG. 10G, prosthetic socket 10 is positioned in the exact position and alignment as trial 30 was when trial 30 was properly positioned in bone cavity 12.

In placing prosthetic socket 10 according to embodiments of the invention, peg 101 of prosthetic socket 10 is placed in peg positioning bore 14 in process 910. Driving plate 913 of physical guide 91 may be used to align prosthetic socket 10 as peg 101 is being fitted in peg positioning bore 14. At this point, prosthetic socket 10 is loosely engaged to bone 13.

In process 911 of the illustrated embodiment, a force is applied to driving plate 913 of physical guide 91 to drive prosthetic socket 10 firmly into peg positioning bore 14 at the same angle trial 30 was when it was fitted in bone cavity 12, as shown in FIG. 10G. Directional guidance is provided according to embodiments by physical guide 60 and/or visual guide 110. It should be noted that peg 101 does not need to be cannulated and, thus, in some embodiments there is no lumen in peg 101.

Figure 10H:
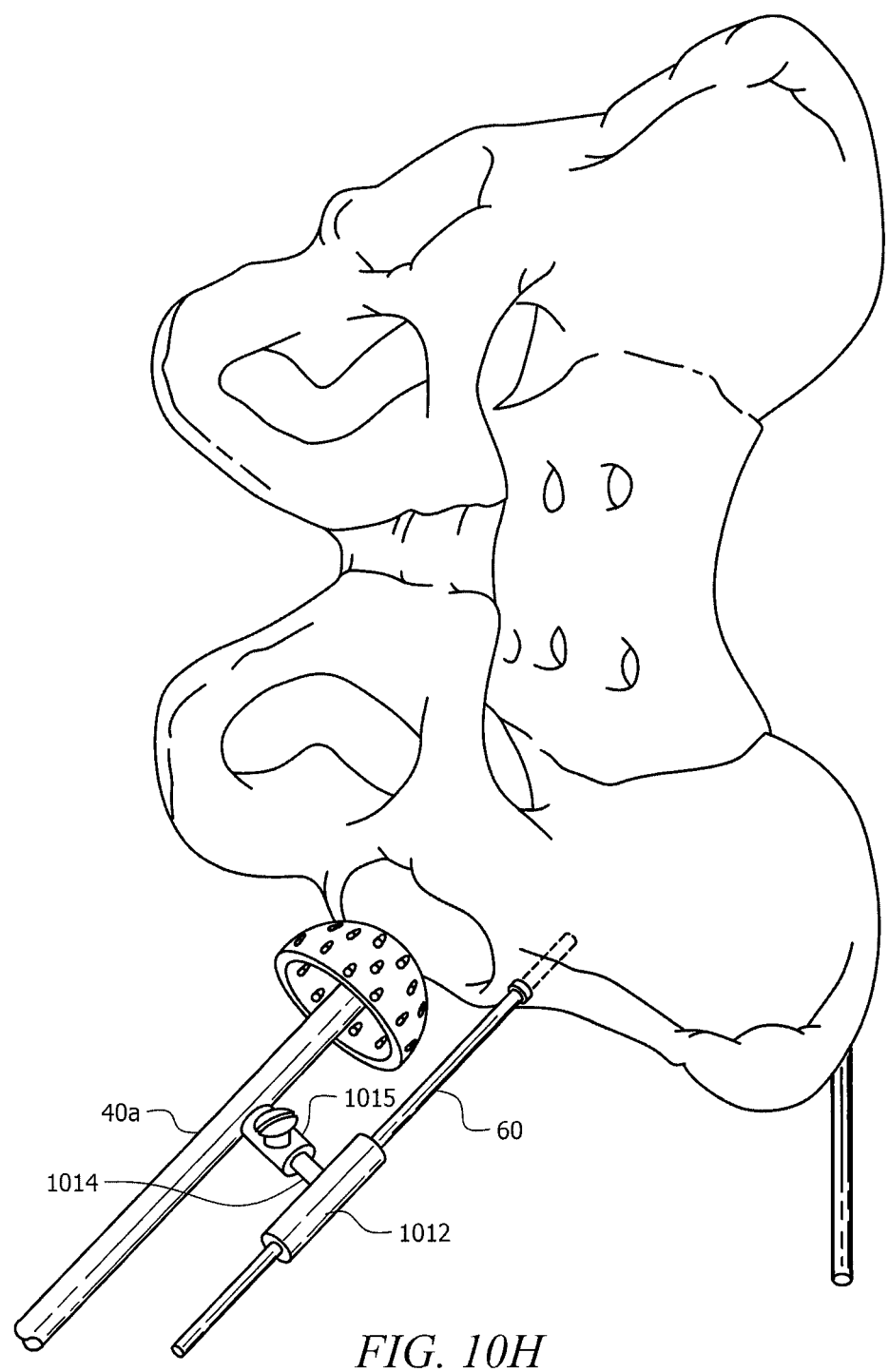
FIG. 10H show operation of guide devices used to guide a reamer according to an embodiment of the invention.

It should be appreciated that various combinations of features and guides may be utilized according to embodiments in disposing a prosthetic device in a desired orientation. For example, features, such as the peg and peg bore described above, may be omitted according to embodiments. Likewise, combinations of visual guides, physical guide, and reference guides different than discussed with respect to flows 20 and 90 above may be utilized according to embodiments of the invention. Directing attention to FIG. 10H, an embodiment wherein physical guide 60 is utilized (in addition to or in alternative to using visual guide 110) to provide guidance with respect to operation of reamer 40a is shown. Specifically, tubular pin guide 1012 is fixedly attached to reamer 40a by connectors 1014 and 1015. Physical guide 60 is inserted through tubular pin guide 1012 to provide guidance during operation of reamer 40a.

Although a same visual guide 110 has been referenced with respect to various tools and devices used in a prosthetic implant procedures above, it should be appreciated that different visual guides may be utilized with respect to some or all such tools and devices. For example, a particular visual guide configuration adapted for guidance in a particular plane or planes may be utilized with respect to a first tool and a different visual guide configuration adapted for guidance in a different plane or planes may be utilized with respect to a second tool in operation of flows 20 and 90 discussed above.

Figure 15:
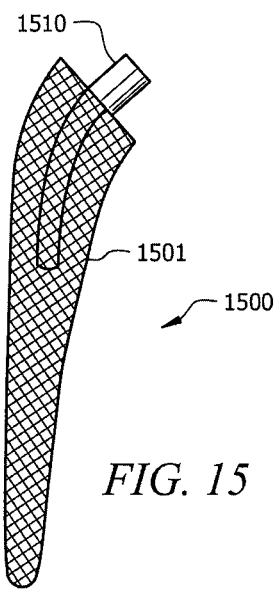
FIG. 15 shows a visual guide of an embodiment of the invention.

Guide configurations different than those shown with respect to the embodiments discussed above may be utilized according to embodiments of the invention. For example, broach 1500 shown in FIG. 15 provides an embodiment of a visual guide adapted for determining the angle of the femoral neck. Accordingly, broach 1500 may be utilized according to embodiments to facilitate the proper positioning of a prosthetic ball (e.g., prosthetic ball 11 of FIG. 1A) on the femur to correspond with the placement of a prosthetic socket in a pelvis.

The femoral neck has a slightly forward position from the shaft of the femur. It is desirable to properly maintain this forward position in order to maintain the hip geometry after the prosthetic implant. Broach 1500 of the illustrated embodiment is adapted to provide guidance with respect to the femoral neck configuration for proper placement of a prosthetic ball. Accordingly, broach 1500 of the illustrated embodiment comprises visual guide 1510, disposed upon body 1501, for providing guidance to a medical practitioner regarding the desired position of the prosthetic ball.

Figure 16A:
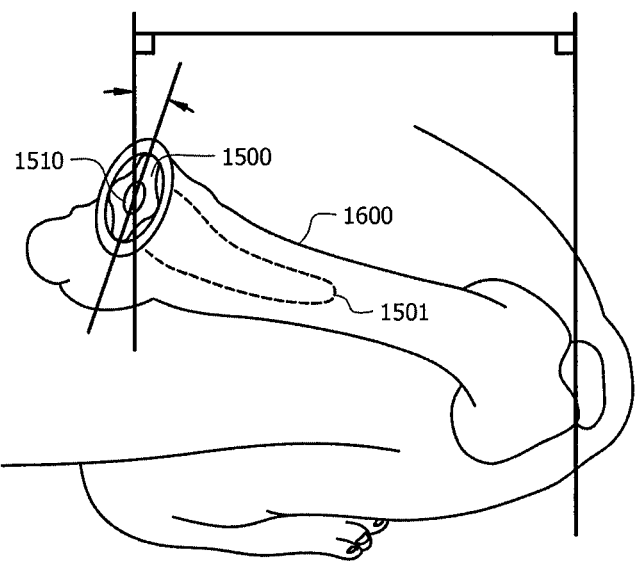
FIGS. 16A and 16B show the use of the visual guide of FIG. 15 according to embodiments of the invention.
Figure 16B:
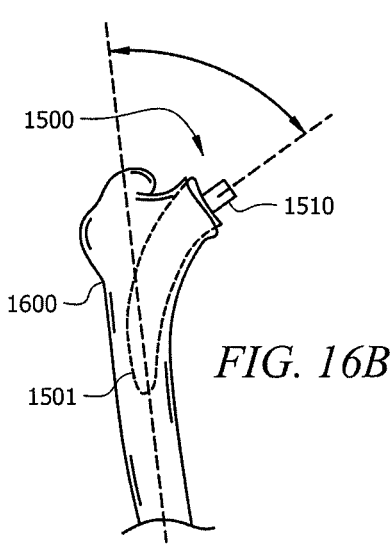

FIGS. 16A and 16B show broach 1500 utilized with respect to femur 1600 to provide information regarding the desired angle of rotation and tilt for placing prosthetic ball 11 on femur 1600. Femur 1600 shown in FIGS. 16A and 16B has had the femoral head and neck have removed in preparation for the prosthetic implant. Broach 1500 is placed in femur 1600 such that body 1501 thereof rests in the medullary cavity. Body 1501 is shaped to follow the walls of the medullary cavity such that broach 1500 is oriented in accordance with the natural geometry of femur 1600. Thus, visual guide 1510 extending from femur 1600 when broach 1500 is placed therein provides an indication of the angle of adduction (FIG. 16A) and the angle of anteversion (FIG. 16B) of the femoral head and neck.

Visual guide 1510 may comprise a trunnion protruding from body 1501 from which one or more angles are measured. Such angles may be referenced off of the knee cap using broach 1500, as shown in FIG. 16A. Visual guide 1510 may additionally or alternatively comprise a tilt sensor, a goniometer, etc. providing a visual indication of the aforementioned angles.

The information provided through use of broach 1500 of embodiments may be utilized by a medical practitioner in placing prosthetic ball 11 on femur 1600 after removal of broach 1500 therefrom. For example, the angle of adduction and/or angle of anteversion determined using broach 1500 may be used for orienting prosthetic ball 11.

Moreover, the information provided through use of broach 1500 may be utilized in placing other prosthetic devices. If there is excessive anteversion in the femur, for example, this can be taken into consideration when positioning prosthetic socket 10. For example, the femoral head and neck typically have approximately 12-14° of anteversion (forward tilt). If, however, the angle of anteversion is determined to be appreciably greater (e.g., 20° or greater) than this normal range using broach 1500 the position of prosthetic socket 10 may be altered to compensate and to insure stability of the hip.

In embodiments of the invention, various prosthetic alignment devices such as trial 30, drill 40, physical guide 50, physical guide 80, physical guide 91, and broach 1500 are disclosed as comprising a guide device, such as visual guide 110. Because trial 30, drill 40, physical guide 50, physical guide 80 and physical guide 91 are to be sterile when initially used on a patient, these devices may be either disposable or capable of undergoing sterilization by heat, chemicals and the like. In the cases where the host devices are capable of being sterilized, guide devices of embodiments may be detachable from the host device. For example, the sterilization process may destroy or otherwise adversely affect the components of a visual guide device, depending on the configuration and sterilization method used. In a case where a component of a guide device would be destroyed by sterilization, the guide device or portions thereof may be discarded after use to avoid contamination of the sterile field from subsequent use.

In other embodiments, the guide devices may be configured to undergo certain types of sterilization and thus may remain attached where a host device is subject to such a sterilization technique. Alternatively, the guide device may be detached from the host device to allow sterilization of the guide device using an appropriate sterilization technique and then reused with the host device which may have been sterilized by a different process. Guide devices may be made detachable from a host device by, for example, providing a cavity in the host device properly sized so that the guide device may be snapped into the cavity prior to surgery and later pried out of the cavity after surgery.

Figure 12:
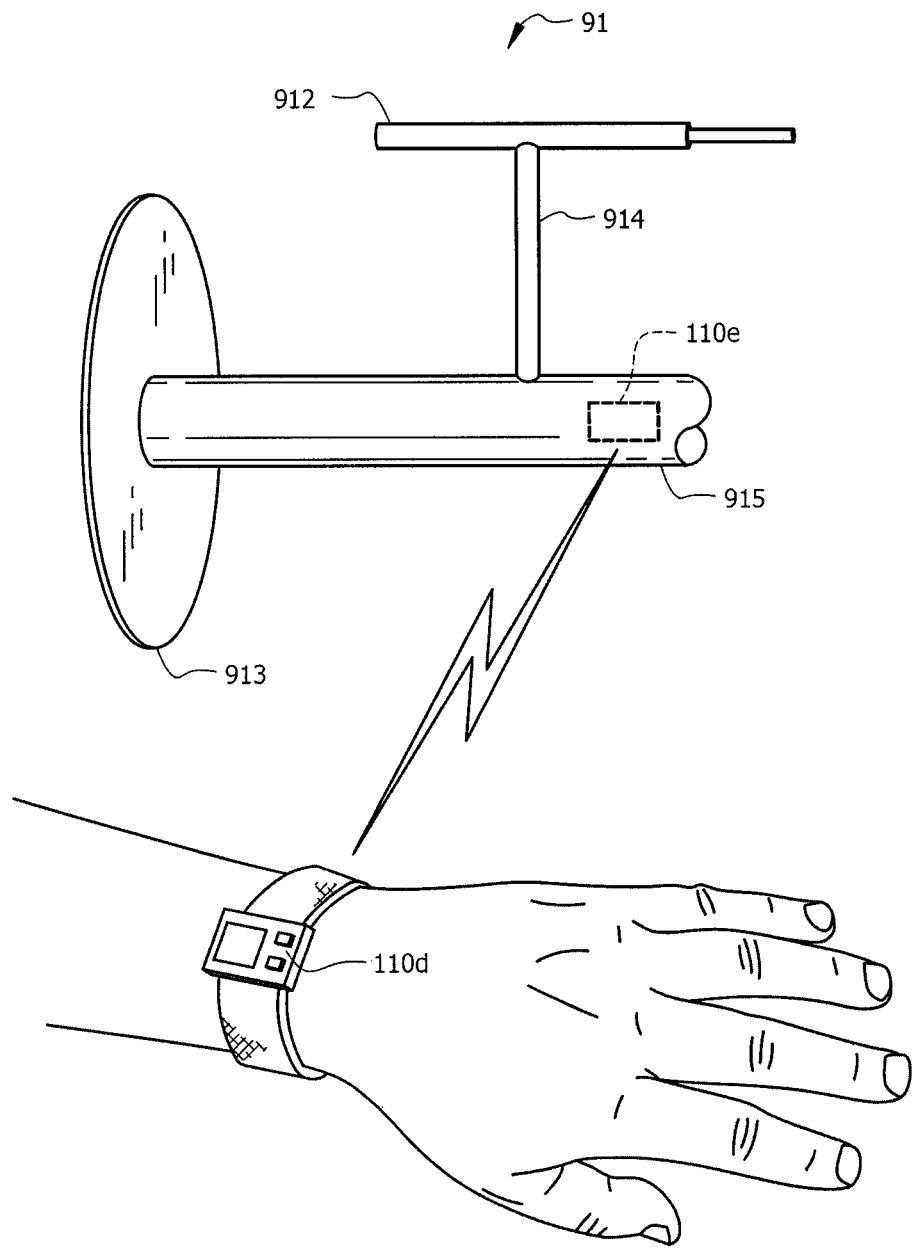
FIG. 12 shows a distributed visual guide configuration according to embodiments of the invention.

In one embodiment of the invention, to avoid the discarding of the guide devices, a guide device is divided in two parts. For example, an embodiment of visual guide 110 comprising a tilt sensing device may be divided into tilt sensing device electronics 110E comprising a transmitter and display 110D comprising a receiver, as shown in FIG. 12. Tilt sensing device electronics 110E is capable of transmitting data to display 110D to cause display 110D to display the angle measured by tilt sensing device electronics 110E, though display 110D and tilt sensing device electronics 110E are apart from each other. Tilt sensing device electronics 110E of embodiments is completely enclosed in a host device, such as physical guide 91. Thus tilt sensing device electronics 110E is protected from heat and chemicals etc. during the sterilization of physical guide 91. Display 110D is remote from physical guide 91 and would not need sterilization as it is not placed in a patient's body. Instead, display 110D is placed in a location visible to the medical practitioner carrying out the hip replacement procedure but remote from sensing device electronics 110E.

In one embodiment, display 110D is configured to be worn on a medical practitioner's wrist. In another embodiment, display 110D is located on other operating room equipment that has patient monitors or in any other location in the operating room convenient to the medical practitioner. In some embodiments, though visual guide 110 has both sensing device electronics and display in one unit, visual guide 110 may be capable of transmitting data to a second display remote from visual guide 110. Such second display may be located on other operating room equipment that has patient monitors.

It should be noted that the methods, devices and systems described herein are applicable to surgeries at different locations of the body. For example, the procedures described herein may be used in surgeries such as hip replacement surgery, shoulder replacement surgery and knee replacement surgery. Further, the methods, devices and systems include surgeries on humans and surgeries performed in the field of veterinary medicine.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method for properly orienting a prosthetic socket in a bone cavity of a patient, said method comprising the following steps in the sequence set forth: (a) establishing a reference guide providing a baseline reference with respect to the patient; (b) removing unwanted bone material from said bone cavity under guidance of a guide, wherein said guide is used to guide an orientation of a reamer during said removing to provide a prepared bone cavity for properly orienting said prosthetic socket; (c) orienting a trial in said bone cavity, wherein said trial includes a central drill guide channel and said orienting comprises drilling a peg positioning bore into said bone corresponding to said guide channel, said drill guide channel adapted to define an angle of said peg positioning bore being drilled into said bone; (d) placing a guide piece, according to the orientation of said trial, in a bone proximate to said bone cavity, when said trial is in a desired position by fitting a drill guide into said peg positioning bore, wherein said drill guide has a cannulated tube and a cannulated sleeve, and inserting said guide piece through said cannulated tube of said drill guide into said proximate bone, wherein the angle in which said guide piece is placed into said bone is defined by the position of said drill guide in said peg positioning bore; and (e) orienting said prosthetic socket into said bone cavity using said guide piece's position and alignment for guidance, wherein a cannulated portion of a peg is adapted to fit over said guide piece and, wherein at least one of said removing unwanted bone material from bone cavity, said orienting said trial, said placing said guide piece, and said orienting said prosthetic socket is performed using reference to said reference guide, wherein at least one visual guide is used to aid in positioning and aligning of at least one of said reference guide, said drill guide, said reamer, said trial and said prosthetic socket, wherein said at least one visual guide comprises a tilt sensor device.

2. The method of claim 1, wherein said establishing said reference guide is performed prior to any surgical steps for implanting said prosthetic socket.

3. The method of claim 1, wherein said reference guide comprises a guide piece disposed in said patient in a specific orientation, wherein said reference to said reference guide confirms that said reference guide remains in said specific orientation.

4. The method of claim 1, wherein said reference guide comprises a guide piece disposed in said patient in a specific position, wherein said reference to said reference guide comprises making a measurement using said specific position as a reference.

5. The method of claim 1, wherein said visual guide is disposed on a power head used to drive said reamer.

6. The method of claim 1 further comprising using a driver having visual guide, said driver adapted to be used to position said trial.

7. The method of claim 1, wherein said drill guide channel may be removably attached to said trial.

8. The method of claim 1 further comprising using a prosthetic socket driver having a visual guide and an aperture operable to receive said guide piece.

9. A method for properly orienting a prosthetic socket in a bone cavity of a patient, said method comprising: establishing a reference guide providing a baseline reference with respect to the patient; orienting a trial in said bone cavity by using a guiding device, wherein said trial includes a central drill guide channel, said guiding device having a driving plate, a modular extension and a tubular pin guide, wherein said tubular pin guide is adopted to receive a guide piece, wherein an angle in which said guide piece is placed into a bone is defined by a position of said modular extension of said guide device in a peg positioning bore, said guide piece being precisely parallel to said peg positioning bore, wherein said drill guide channel is adapted to define an angle of said peg positioning bore being drilled in said bone proximate to said bone cavity; and orienting said prosthetic socket into said bone cavity using said guiding device, wherein said guide piece of said guiding device provides directional guidance for said driving plate, wherein said driving plate is adapted to guide said prosthetic socket, when said driving plate is positioned over said prosthetic socket to drive it in said bone cavity, wherein at least one visual guide is used to aid in positioning and aligning of at least one of said reference guide, said guiding device, said trial and said prosthetic socket, wherein said at least one visual guide comprises a tilt sensor device.

10. The method of claim 9 further comprising removing unwanted bone material from bone cavity under guidance of a guide, wherein said guide is used to guide an orientation of a reamer during said removing to provide a prepared bone cavity for properly orienting said prosthetic socket.

11. The method of claim 10 wherein at least one of said removing unwanted bone material from bone cavity, said orienting said trial, said drilling said peg positioning bore, said placing said guide piece, and said orienting said prosthetic socket is performed using reference to said reference guide.

* * * * *